US012018242B2

United States Patent
Brillmann et al.

(10) Patent No.: US 12,018,242 B2
(45) Date of Patent: Jun. 25, 2024

(54) BIOREACTORS FOR ROOT ORGAN CULTURES

(71) Applicant: Evologic Technologies GmbH, Vienna (AT)

(72) Inventors: Markus Brillmann, Vienna (AT); Paul Krautwaschl, Vienna (AT); Wieland Reichelt, Vienna (AT); Christoph Herwig, Vienna (AT)

(73) Assignee: Evologic Technologies GmbH, Vienna (AT)

( * ) Notice: Subject to any disclaimer, the term of this patent is extended or adjusted under 35 U.S.C. 154(b) by 842 days.

(21) Appl. No.: 16/956,888

(22) PCT Filed: Dec. 21, 2018

(86) PCT No.: PCT/EP2018/086806
§ 371 (c)(1),
(2) Date: Jun. 22, 2020

(87) PCT Pub. No.: WO2019/122437
PCT Pub. Date: Jun. 27, 2019

(65) Prior Publication Data
US 2021/0155891 A1 May 27, 2021

(30) Foreign Application Priority Data

Dec. 22, 2017 (EP) ..................... 17210469
Mar. 16, 2018 (EP) ..................... 18162293

(51) Int. Cl.
*C12M 1/33* (2006.01)
*C12M 1/00* (2006.01)
(Continued)

(52) U.S. Cl.
CPC ............ *C12M 45/02* (2013.01); *C12M 25/16* (2013.01); *C12M 27/02* (2013.01); *C12M 29/06* (2013.01);
(Continued)

(58) Field of Classification Search
None
See application file for complete search history.

(56) References Cited

U.S. PATENT DOCUMENTS

2002/0076815 A1* 6/2002 Banerjee ................. C12M 29/06
435/400
2002/0110915 A1* 8/2002 Shaaltiel ................. C12M 29/00
435/296.1
2014/0004571 A1* 1/2014 Garrett .................... C12P 19/14
435/99

FOREIGN PATENT DOCUMENTS

CN 102408991 A * 4/2012 ............ C12M 23/58
KR 100671010 B1 * 9/2006 ............ C12M 21/08
(Continued)

OTHER PUBLICATIONS

Berry et al. "Characterisation of stresses on microcarriers in a stirred bioreactor." Applied Mathematical Modelling 40 (2016) 6787-6804. (Year: 2016).*
(Continued)

*Primary Examiner* — William H. Beisner
(74) *Attorney, Agent, or Firm* — Leydig, Voit & Mayer, Ltd.

(57) ABSTRACT

The present invention relates to bioreactors for root organ cultures that enable large parts of the inoculation or biomass transfer, cultivation and harvest of the cultures to be performed outside of an aseptic environment. The present invention further relates to methods of producing and aseptically harvesting roots, and methods of producing root cultures using the aforementioned bioreactors alone or as
(Continued)

part of an apparatus further comprising an inoculation vessel or at least one further bioreactor.

16 Claims, 10 Drawing Sheets

(51) Int. Cl.
    *C12M 1/06*     (2006.01)
    *C12M 1/12*     (2006.01)
    *C12M 1/26*     (2006.01)
    *C12M 1/34*     (2006.01)
    *C12N 5/04*     (2006.01)

(52) U.S. Cl.
    CPC ............ *C12M 33/00* (2013.01); *C12M 41/00* (2013.01); *C12M 41/26* (2013.01); *C12M 41/32* (2013.01); *C12N 5/04* (2013.01)

(56) References Cited

FOREIGN PATENT DOCUMENTS

WO     WO 1989/010958 A1     11/1989
WO     WO 2017/207822 A1     12/2017

OTHER PUBLICATIONS

Hilton et al. "Growth and hyoscyamine production of 'hairy root' cultures of Datura stramonium in a modified stirred tank reactor." Appl Microbiol Biotechnol (1990) 33 : 132-138. (Year: 1990).*
Choi et al., "Pilot-scale culture of adventitious roots of ginseng in a bioreactor system." *Plant Cell, Tissue and Organ Culture*, 62(3): 187-193 (Jan. 1, 2000).
Iit Guwahati, "Application of Cell Culture Systems in Metabolic Engineering" (Oct. 3, 2012) [downloaded from https://nptel.ac.in/courses/102103016/36# on Sep. 11, 2018].
Krombholz et al., "Production of Forskolin by Axenic *Coleus forskohlii* Roots Cultivated in Shake Flasks and 20-I Glass Jar Bioreactors," *Planta Medica*, 58(04): 328-333 (Aug. 1, 1992).
Paek et al., "Application of bioreactor systems for large scale production of horticultural and medicinal plants," *Plant Cell, Tissue and Organ Culture*, 81(3): 287-300 (Jun. 1, 2005).
European Patent Office, International Search Report in International Patent Application No. PCT/EP2018/086806 (dated Feb. 12, 2019).
European Patent Office, Written Opinion in International Patent Application No. PCT/EP2018/086806 (dated Feb. 12, 2019).
Ramakrishnan et al. "Inoculation and Tissue Distribution in Pilot-Scale Plant Root Culture Bioreactors," *Biotechnology Techniques*, 8(9): 639-644 (1994).
Wilson et al., "The Cultivation of Transformed Roots from Laboratory to Pilot Plant," Progress in *Plant Cellular and Molecular Biology*, Springer, Dordrecht, pp. 700-705 (1990).
China National Intellectual Property Administration, First Office Action in Chinese Patent Application No. 201880083256.X (dated Apr. 15, 2023).

* cited by examiner

BIOREACTORS FOR ROOT ORGAN CULTURES

CROSS-REFERENCE TO RELATED APPLICATIONS

This application is the U.S. national phase of International Patent Application No. PCT/EP2018/086806, filed Dec. 21, 2018, which claims the benefit of European Patent Application No. 17210469.7, filed Dec. 22, 2017, and European Patent Application No. 18162293.7, filed Mar. 16, 2018, all of which are hereby incorporated by reference in their entireties herein.

FIELD OF THE INVENTION

The present invention relates to bioreactors for root organ cultures that enable large parts of the inoculation or biomass transfer, cultivation and harvest of the cultures to be performed outside of an aseptic environment. The present invention further relates to methods of producing and aseptically harvesting roots and methods of producing root organ cultures using the aforementioned bioreactors alone or as part of an apparatus further comprising an inoculation vessel or at least one further bioreactor.

BACKGROUND OF THE INVENTION

The production of root organ cultures offers access to plant tissue derived compounds, while circumventing the common drawbacks of sourcing plant derived compounds from the field. In a bioreactor, all environmental factors can be controlled within narrow ranges. This benefit allows flexible, reproducible and predictable harvests of biomass to derive economically relevant compounds e.g. secondary plant metabolites. Root organ cultures are commonly independent of photosynthesis and sequester all necessary nutrients from the media. However, root organ cultures differentiated into hairy roots and into adventitious roots.

Hairy roots are derived from plant material transformed with *Agrobacterium rhizogenes*. Upon transformation, the plant tissue grows in thin roots, without further differentiation into different tissue types. Hairy root cultures can be used to produce high value secondary plant metabolites in liquid cultures, using their set of metabolic pathways or plant origin. Amongst the metabolites and other valuable products are dyes, flavors, pesticides and pharmaceuticals. Root organ cultures in general are genetically stable long term cultures, and hairy root cultures are especially advantageous due to the rapid growth exhibited by hairy roots that is often comparable to suspended non-plant eukaryotic cell culture growth rates. Importantly, as opposed to these other suspension cultures, hairy root cultures do not require the addition of growth regulating factors to the culture.

However, large scale cultures of hairy roots present several problems due to the morphology of these roots. Specifically, hairy roots have the principal morphological features of normal plant roots, which means that they are adopted to growth on solid media. Accordingly, they attach to each other when grown in liquid cultures and form dense root clumps upon prolonged growth in liquid media. Due to these root clumps, difficulties in handling hairy root cultures arise already during inoculation, the very first step of production processes in bioreactors.

Cell suspension cultures of prokaryotic or other eukaryotic organisms can easily be transferred between vessels for inoculation, where the transfer between vessels or compartments of vessels via tubes and pipes is almost independent of the respective biomass concentration. In contrast, hairy root clumps increase in size as the biomass of the culture continues to grow. Therefore, a higher biomass concentration in the inoculum used to inoculate larger cultures impacts technical design aspects of suitable inoculation vessels and bioreactors in terms of inoculation tubes, pipes and ports. Consequently, the growth morphology massively limits the design space for technical equipment for hairy root based production processes during scale up from laboratory to industrial scale cultures.

These challenges have only been partially addressed so far. The standard procedure used in laboratory scale hairy root cultures is the manual dissection of the root clumps followed subsequently by manual transfer of the resulting root pieces to a bioreactor. Therefore, the inoculation vessel and bioreactor are commonly opened inside an aseptic environment, e.g. in a laminar flow bench, in order to manually transfer the root pieces without contaminating the culture. However, this approach is hardly scalable to industrial production volumes.

The first steps towards a scalable solution for bioreactor inoculation with hairy root cultures were made by Ramakrishnan et al. (1994, Biotechnology techniques 8(9): 639-644). They used a sterilized blender to homogenize the roots of a pre-culture to prepare an inoculum. The resulting slurry was then filtered, blotted, and transferred via a 4 L transfer vessel into a 16.68 L bioreactor via positive displacement using compressed air. However, the steps of cutting, filtering, blotting, and filling of the transfer vessel all had to be performed in an aseptic environment, which, like manual transfer, limits the scalability of this approach.

Wilson et al. (1990, Progress in Plant Cellular and Molecular Biology, pp. 700-705; and WO 89/10958) was able to inoculate a 500 L pilot scale bioreactor using a dedicated inoculation vessel flanged to the top of the 500 L bioreactor. Nevertheless, the inoculation of this smaller inoculation vessel also had to be performed in an aseptic environment with root pieces dissected in an aseptic environment as well. Aside from this, the question of scaling up from 500 L to industrial scale culture volumes remains elusive, and no reports of scalable solutions to hairy root culture inoculation or transfer for the purpose of reactor inoculation have been made.

The harvest of hairy root cultures after inoculating a bioreactor and cultivating the hairy root culture in said bioreactor faces a similar set of problems with regard to scalability. The morphological features of hairy root cultures pre-determine the necessary reactor specifications. As already mentioned, hairy roots entangle and form clumps upon growth associated length increase and root branching. Upon further growth, the root clumps become bigger and denser, up to a point where the outermost roots of the clump restrict nutrient, metabolite, and oxygen exchange with the inner parts of the clumps. The result is a decrease in observed biomass growth caused by death by starvation of generally viable roots. Consequently, state of the art reactors generally share some kind of solid attachment matrix for hairy root growth. These matrices increase the biomass distribution over the reactor volume. With a better biomass distribution, root clump density is decreased and root death is minimized (see e.g. WO 89/10958).

However, problems regarding scalability of these reactor systems arise with volumes greater than 100-500 L, regarded as "pilot scale" in bioprocess engineering. For reactor harvest and transfer to bigger production reactors (called seed train), the biomass first has to be detached from the attachment matrix, and subsequently has to be moved to a bigger reactor. During these necessary steps, contamination of any kind must be avoided, i.e. these steps must be performed under aseptic conditions, e.g. by using laminar flow, which makes them time costly, difficult, and expensive to achieve.

The reactors of the prior art suitable for hairy root cultures all require the provision of an aseptic environment for their operation, e.g. by use of clean room technology, in order to maintain sterility upon harvest, as large openings in the reactor vessel have to be opened for manual harvest of the root culture. An automated, aseptic transfer of the harvested hairy root culture into a bigger reactor vessel (seed train) or for extraction of the desirable secondary metabolites has not been described.

What is more, the 500 L reactor project of Wilson et al. described above was shut down in the early 2000s as a result of sterility problems.

To summarize, when trying to achieve large scale hairy root cultures, two central problems exist: inoculating a bioreactor, i.e. cutting, optionally washing, and transferring viable hairy root biomass to a large scale culture, and producing and aseptically harvesting hairy roots from a large scale culture, i.e. detaching hairy roots from an attachment matrix, cutting them, and optionally transferring them into a larger volume culture both require manual work under expensive and, at large scale, impractical aseptic, e.g. clean room, conditions.

Accordingly, there is a need for alternative inoculation vessels and bioreactors for hairy root cultures of all scales that enable the automation of the above mentioned processes and do not require an aseptic environment.

Adventitious roots, like hairy roots, are plant tissues that can be used in root organ cultures for the production of industrially relevant secondary metabolites. While both share the phenotypical root growth, this growth is induced by different triggers. As described above, hairy roots are established using *Agrobacterium rhizogenes* to transform plant tissue and to elicit the typical hairy root growth. Adventitious roots, in contrast to hairy roots, are established and maintained through the use of plant growth hormones in the culture medium. For the same plant organism, growth rates of hairy and adventitious roots can be comparable in the range of approx. 0.01-0.5 $d^{-1}$. While phenotypical and morphological characteristics are rather comparable between adventitious and hairy roots of the same plant species, physiological characteristics differ greatly. For example, adventitious roots require the continuous supplement of plant growth hormones, while hairy roots are considered genetically stable. In addition, upon cutting the root biomass, the growth rates of hairy roots has been shown to decline (Krombholz et al., Planta Medica 58(34): 328-333, 1 Aug. 1992). In contrast, the growth rate of adventitious roots has been shown to be increased upon cutting roots into pieces (Krombholz et al., Planta Medica 58(34): 328-333 (1 Aug. 1992); Sung et al., Plant Cell, Tissue, and Organ Culture 62(3): 187-193 (1 Jan. 2000); Paek et al., Plant cell, Tissue and Organ Culture 81(3): 287-300 (1 Jun. 2005)).

While the physiology differs, the phenotype of hairy roots cultured in liquid medium resembles the phenotype of adventitious root cultures. In both cultures, the roots elongate and branch throughout the growth period, and therefore display a great tendency to entangle and, consequently, to form clumps. This tendency of clump formation increases with cultivation time and biomass content. These densely packed clumps greatly hinder automated processing. These clumps can reach a packed density where disintegration of the clumps cannot be achieved without use of external mechanical energy (e.g. homogenization). Furthermore, metabolite removal and media, as well as gas exchange, are highly restricted in the center-portion of the clumps, impairing biomass growth. This clump formation and the correlated implications are common denominators for hairy and adventitious root cultures, although the effect of homogenization on the growth rates has been shown to differ between hairy roots and adventitious roots. It follows that hairy roots are more difficult to culture than adventitious roots due to their sensitivity to shear stress. Accordingly, any method or vessel suitable for the cultivation of hairy roots is also suitable for adventitious root cultivation, but the same is not a given for the inverse.

SUMMARY OF THE INVENTION

The inventors have developed bioreactors that are suitable for large scale root organ cultures, enable inoculation, production and aseptic harvest of the root organ culture biomass without requiring an aseptic environment. The inventors have further developed an apparatus comprising such a bioreactor and an inoculation vessel or at least one further bioreactor that enables the processes of cutting and optionally washing roots within the vessel, is further suitable for transferring the so prepared inoculum into a bioreactor, and does not require an aseptic environment for any of these steps.

The object of the present invention is solved by the subject matter of the independent claims. Preferred embodiments are apparent from the dependent claims.

In an embodiment, the invention provides a bioreactor for the cultivation of root organ cultures, comprising:
- a cultivation chamber (2);
- a fast rotatable knife or a rotor stator (6) located at the bottom of the bioreactor;
- an inoculation port (1), wherein the inner diameter of the inoculation port (1) is ≥10 mm;
- a harvest port (5), wherein the inner diameter of the harvest port (5) is ≥10 mm and wherein the harvest port (5) is located at the bottom of the bioreactor; and two aeration outlets (3, 4), wherein one aeration outlet is for gas inlet and the other aeration outlet is for gas outlet.

In an embodiment, the bioreactor further comprises a gas sparger (7). In an embodiment, the bioreactor further comprises one to four outlets for dip tubes (8), wherein the one to four dip tubes (8) are for base addition, feed addition, acid addition, and/or sampling. In an embodiment, the bioreactor further comprises one to three ports for probes (9), wherein the probes are for measuring pH, dissolved oxygen, and/or conductivity. In an embodiment, the cultivation chamber (2) volume is from 1-100000 L.

In one embodiment, the bioreactor further comprises
- an attachment matrix (10a);
- a rotatable attachment matrix mounting (12);
- a vertical shearing blade (11a) for root detachment; and
- a support ring for the shearing blade (13);

wherein the attachment points on the attachment matrix (10a) are vertically arranged, and wherein the attachment matrix (10a) is vertically rotatable on the rotatable attachment matrix mounting (12) and the vertical shearing blade (11a) is static.

In another embodiment, the bioreactor does not comprise an attachment matrix.

In yet another embodiment, the bioreactor further comprises an attachment matrix (10b), wherein the attachment matrix is composed of beads, said beads comprising a polysaccharide and a growth medium. In an embodiment, the polysaccharide is selected from the group consisting of alginate, agarose, and gellan. In an embodiment, the beads have a diameter of 1-5 mm.

In yet another embodiment, the bioreactor further comprises
- an attachment matrix (10c);
- a central, vertical rotary shaft; and
- multiple horizontally arranged detachment knives (11b);

wherein the attachment matrix (10c) is composed of multiple, horizontal root support disks, and wherein said root support disks are spaced in regular distances of ≥7 cm, and wherein the detachment knives (11b) are mounted horizontally on the vertical rotary shaft so that one detachment knife is located at a distance of 0.05-5 mm from each root support disk, and wherein the number of detachment knives (11b) is the same as or larger than the number or root support disks. In an embodiment, the multiple root disks are stainless steel lattices or stainless steel perforated plates. In an embodiment, the bioreactor further comprises
a cylindrical draft tube (14),
wherein the horizontal root support disks are mounted inside of the cylindrical draft tube (14), wherein the draft tube (14) consists of a cylinder that is fully open at its top and bottom ends, and wherein the gas sparger (7) consists of two independently usable sparging elements, one of which (7a) is located beneath the center of the draft tube and the other one of which (7b) is a ring sparger located below or outside the draft tube in the lower half of the cultivation chamber.

The invention also provides for a method of producing and aseptically harvesting roots, comprising the steps of
1) cultivating a root organ culture in a growth medium inside a bioreactor of the invention;
2) optionally detaching the roots of the root organ culture from the attachment matrix (10a, 10b, or 10c) inside the bioreactor;
3) optionally letting the roots settle;
4) cutting the roots inside the bioreactor using the fast rotatable knife or the rotor stator (6) at the bottom of the bioreactor; and
5) removing the cut roots using the harvest port (5);

wherein steps 1-4 are performed inside the bioreactor and wherein steps 1-5 do not require an aseptic environment.

In an embodiment, the cultivating step is performed for 1-12 weeks.

In an embodiment, the detaching step is accomplished by the use of shear force exerted by the shearing blade (11a) on the rotating matrix (10a) of the bioreactor.

In an embodiment, the cultivating step comprises inducing culture medium movement by gassing the root organ culture at 0.2-50 sL/L/h throughout the step of cultivating through the use of the gas sparger (7). In an embodiment, the gassing is done with sterile air with a composition of 21-30% $O_2$, 0.04-2% $CO_2$, and 68-78.96% $N_2$ In an embodiment, the detaching step is accomplished by dissolving the attachment matrix (10b) beads of the bioreactor. In an embodiment, the attachment matrix (10b) beads are dissolved by addition of citric acid or a polysaccharide cleaving enzyme. In an embodiment the citric acid is 10 mM citric acid with a pH of 5-6. In another embodiment, the polysaccharide cleaving enzyme is selected from the group consisting of alginate lyase, gellan lyase, and beta-agarase.

In an embodiment, the detaching step is accomplished by the use of shear force exerted by the detachment blades (11b) rotating above the root support disks of the bioreactor.

In an embodiment, the cutting step is accomplished by rotating the fast rotatable knife (6) at a tip speed of 1-50 m/s or the rotor stator (6) at the bottom of the bioreactor. In an embodiment, the cutting step is performed at a temperature of 0-35° C.

In an embodiment, the removing step is accomplished using a peristaltic pump or chopper pump, or a screw conveyor or by flushing with growth medium.

The invention further provides an apparatus for inoculation, production, and harvest of hairy root cultures, comprising a bioreactor of the invention connected to an inoculation vessel or at least one further bioreactor of the invention.

In one embodiment, the apparatus comprises a first bioreactor of the invention and at least one further bioreactor of the invention, wherein said first bioreactor is connected to said at least one further bioreactor.

Such an apparatus can be used in a method of producing roots, comprising
- a method of preparing an inoculum for a root organ culture from viable root biomass, comprising the following steps:
  1) introducing viable root biomass into the first bioreactor of the apparatus of via the inoculation port (1) in an aseptic environment;
  2) optionally cultivating the introduced root biomass in the presence of a growth medium
  3) optionally cutting the root biomass with the fast rotatable knife or rotor stator (6) of the first bioreacor, optionally wherein the cutting step is performed at a temperature of 0-35° C.,
  4) transferring the cut inoculum from the first bioreactor to the at least one further bioreactor using the harvest port (5) of the first bioreactor and the inoculation port (1) of the at least one further bioreactor,
  optionally wherein the transfer step occurs through a sterile connector, wherein the sterile connector provides minimal flow restrictions and/or wherein the connector imposes minimal cross section reduction of the flow path, optionally wherein the method further comprises a step of flushing the first bioreactor by recirculating growth medium from the at least one further bioreactor to the first bioreactor
  wherein steps 2 and 3 are performed inside the first bioreactor, and wherein steps 2 to 4 do not require an aseptic environment;
  followed by the method of producing and aseptically harvesting roots of the invention performed using the at least one further bioreactor;
- wherein the first bioreactor and the at least one further bioreactor are comprised in the above apparatus.

In another embodiment, the apparatus comprises an inoculation vessel and a bioreactor. In this embodiment, the inoculation vessel is for preparing an inoculum for a root organ culture from viable root biomass, and comprises:
- an inoculation chamber (21)
- a knife (16), wherein the knife is part of a rotatable stirrer blade construction or a knife mill construction and wherein the knife is located within the chamber;
- between three and five outlets from the chamber, wherein the outlets are for root biomass inlet (15), inoculum outlet (17), aeration, media inlet (18, 19), and media outlet, and wherein the inner diameter of the outlets is ≥10 mm.

In an embodiment, the between three and five outlets of the inoculation vessel are used for as few of root biomass inlet, inoculum outlet, aeration, media inlet, and media outlet as possible. In an embodiment, at least one of the three to five outlets of the inoculation vessel can be fitted with a sterile screw cap or sterile rotary seal (20), and the remaining outlets can be fitted with sterile connectors without flow restrictions, which sterile connectors can be connected to tubes. In an embodiment, the outlet for inoculum outlet (17) and/or media outlet is located at the bottom of the inoculation vessel. In an embodiment, the inoculation chamber (21) volume is from 0.2-50 L, preferably from 0.2-2 L. The invention further provides a method of producing root organ cultures, comprising a method of preparing an inoculum followed by a method of producing and aseptically harvesting roots of the invention, wherein an inoculation vessel and a bioreactor of the invention are comprised in the apparatus of the invention.

Such an apparatus can be used in a method of producing roots, comprising a method of preparing an inoculum for a root organ culture from viable root biomass, comprising the following steps:
1) introducing viable root biomass into an inoculation vessel that is part of an apparatus of the invention via one of the three to five outlets in an aseptic environment;
2) cutting the root biomass with the knife (16) of the inoculation vessel;
3) optionally washing the cut root biomass with a washing medium using one or more of the three to five outlet(s) of the inoculation vessel for media inlet and media outlet; and
4) transferring the cut and optionally washed inoculum from the inoculation vessel to a bioreactor using one of the three to five outlets for inoculum outlet (17);
wherein steps 2 and 3 are performed inside the inoculation vessel, and wherein steps 2 to 4 do not require an aseptic environment, followed by a method of producing and aseptically harvesting roots of the invention.

In an embodiment, the cutting step of this method is performed by rotating the knife (16) of the rotatable stirrer blade construction with a tip speed of 1-50 m/s, or rotating the knife of the knife mill construction to exert shear force. In an embodiment, the cutting step is performed at a temperature of 0-35° C.

In an embodiment, the washing medium is selected from the group of a saline solution, a growth medium, and a buffer solution. In an embodiment, the washing medium is added to the inoculation vessel to resuspend the cut root biomass via one of the three to five outlets and wherein the washing medium is removed from the inoculation medium via one of the three to five outlets. In an embodiment, the removal of the washing medium occurs via pouring, pumping, gravitation, or applying overpressure.

In an embodiment, the transfer step occurs through a sterile connector, wherein the sterile connector provides minimal flow restrictions and/or wherein the connector imposes minimal cross section reduction of the flow path.

DETAILED DESCRIPTION OF THE INVENTION

Figure 1:
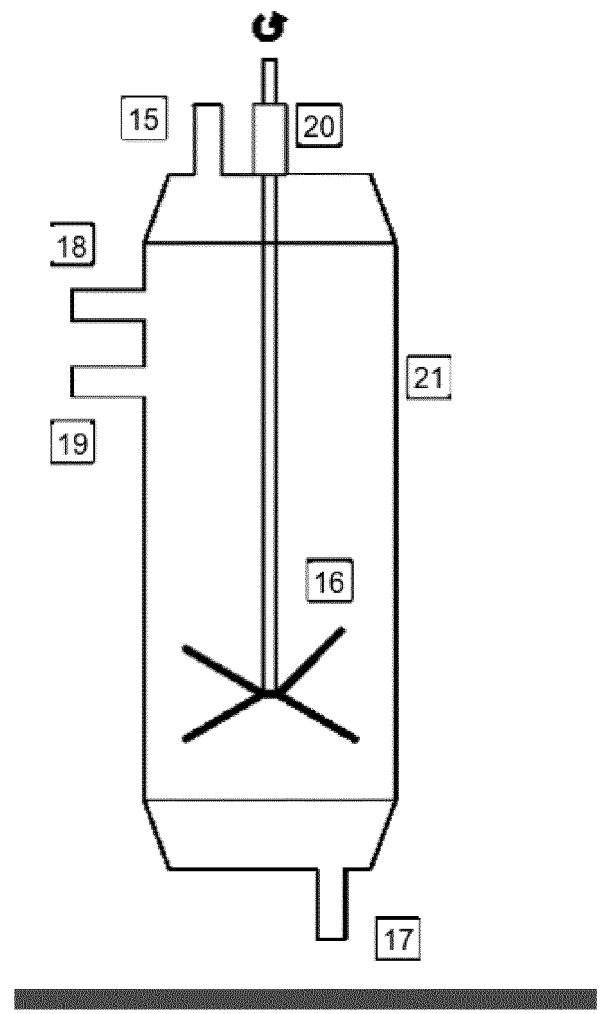
FIG. 1 shows an inoculation vessel for the preparation of a root inoculum from viable hairy root biomass, comprising a hairy root biomass inlet (15), a knife (16), an inoculum outlet (17), outlets for medium inlet, aeration (18, 19), and medium outlet, a rotary seal mount (20) with an outlet for the rotary stirrer shaft of the knife, and an inoculation chamber (21).

The present invention, as illustratively described in the following, may suitably be practiced in the absence of any element or elements, limitation or limitations, not specifically disclosed herein.

The present invention will be described with respect to particular embodiments, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

The term "aseptic environment" as used herein refers to conditions that prevent contamination with microorganisms by being free from microorganisms or having reduced numbers of microorganisms compared to the surrounding environment, with the maximal number of colony forming units per cubic meter ($CFU/m^3$) being 200 (see EU GMP guidelines, clean room classification D). An aseptic environment can be, e.g., a clean room, a laminar flow bench, or a sterile space.

The term "root" as used herein refers to any plant root suitable for stable root organ culture. Especially preferred roots are hairy roots and adventitious roots.

The term "hairy root" as used herein refers to roots derived from plant material transformed with *Agrobacterium rhizogenes*. Upon transformation, the plant tissue grows in thin roots that resemble hair, without further differentiation into different tissue types.

The term "adventitious root" as used herein refers to roots derived from plant material through the use of plant growth hormones. To maintain adventitious root growth in a in-vitro culture, the culture medium must continuously be supplemented with and/or continuously contain plant growth hormones. The plant tissue then grows in thin roots without further differentiation into different tissue types in the culture medium.

The terms "culture", "culturing", "cultivation", and "cultivating" as used herein refer to the production of root material by incubation at conditions suitable to elicit an increase in biomass and to ensure viability of the root material. Preferably, all necessary nutrients are supplied to the roots in a liquid growth medium. The liquid growth medium can either be applied to the root material intermittently from above, e.g. by spraying or trickling, or the root material can be intermittently of continuously submerged therein. Accordingly, a liquid culture of root material can be, e.g., a submersion culture or a trickle-bed culture. Root organ cultures according to the present invention are maintained within bioreactors. Culture duration can span 1 to 12 weeks. In some embodiments, the culture is a batch culture, a fed batch culture, or a batch culture followed by fed batch culture.

The term "submersion culture" as used herein refers to culturing roots by entirely submerging them in liquid growth medium throughout the duration of the culture.

The term "trickle-bed culture" as used herein refers to culturing roots by trickling liquid growth medium onto the roots from above, so that the medium will cover the roots and then trickle down further. In this fashion, the roots are continuously or intermittently coated with a thin film of liquid growth medium. This permits better gas exchange than submersion in large volumes of liquid growth medium.

The term "root biomass" as used herein refers to any viable roots. Preferably, the root biomass is a root pre-culture. The term "pre-culture" as used herein refers to a small scale culture of root material in which the root material is passaged into fresh growth medium several times to increase the total biomass and/or to increase biomass density.

The terms "growth medium" and "culture medium" as used herein refers to a culture medium suitable to facilitate growth of root organ cultures. The growth media of the present invention is typically a liquid growth medium, but may in certain embodiments also be solidified or semi-solidified by addition of polysaccharides. The growth media of the present invention will comprise the constituents listed in Table 1 at concentrations equal to or larger than the minimum concentration and smaller than or equal to the maximum concentration listed in Table 1. Preferred growth media are Schenk and Hildebrandt medium ("SH medium"), Woody Plant medium ("WPM"), B5 medium, Murashige-Skoog medium ("MS medium"), Strullu and Romand medium ("SR medium"), modified Strullu and Romand medium ("MSR medium"), and Minimal medium of Becard and Fortin ("M medium").

TABLE 1

| Constituent | maximum concentration [mmol/L] | minimum concentration [mmol/L] |
| --- | --- | --- |
| $KNO_3$ | 2.47E+01 | 7.52E−01 |
| $NH_4NO_3$ | 2.06E+01 | 0.00E+00 |
| $NH_4H_2PO_4$ | 2.61E+00 | 0.00E+00 |
| $(NH_4)_6Mo_7O_{24} \cdot 4H_2O$ | 1.94E−04 | 0.00E+00 |
| $(NH_4)_2SO_4$ | 1.01E+00 | 0.00E+00 |
| $MgSO_4 \cdot 7H_2O$ | 3.00E+00 | 1.01E+00 |
| $Ca(NO_3)_2 \cdot 4H_2O$ | 1.52E+00 | 0.00E+00 |
| $CaCl_2 \cdot 2H_2O$ | 2.99E+00 | 0.00E+00 |
| $KH_2PO_4$ | 1.25E+00 | 0.00E+00 |
| $NaH_2PO_4 \cdot H_2O$ | 1.09E+00 | 0.00E+00 |
| $MnSO_4 \cdot H_2O$ | 5.92E−02 | 0.00E+00 |
| $MnCl_2 \cdot 4H_2O$ | 1.24E−02 | 0.00E+00 |
| $MnSO_4 \cdot 4H_2O$ | 1.00E−01 | 0.00E+00 |
| KCl | 8.72E−01 | 0.00E+00 |
| KI | 6.02E−03 | 0.00E+00 |
| $H_3BO_3$ | 1.00E−01 | 3.01E−02 |
| $ZnSO_4 \cdot 7H_2O$ | 2.99E−02 | 1.01E−02 |
| $CuSO_4 \cdot 5H_2O$ | 8.01E−04 | 1.00E−04 |
| $Na_2MoO_4 \cdot 2H_2O$ | 1.03E−03 | 9.92E−06 |
| $CoCl_2 \cdot 6H_2O$ | 4.20E−04 | 0.00E+00 |
| $FeSO_4 \cdot 7H_2O$ | 1.00E−01 | 0.00E+00 |
| NaFeEDTA | 2.18E−02 | 0.00E+00 |
| $Na_2EDTA$ | 1.11E−01 | 0.00E+00 |
| Biotin | 3.68E−06 | 0.00E+00 |
| Ca Pantothenate | 3.78E−03 | 0.00E+00 |
| Nicotinic acid | 4.06E−03 | 4.06E−03 |
| Pyridoxine-HCl | 5.91E−03 | 2.96E−03 |
| Thiamine-HCl | 2.96E−02 | 2.96E−04 |
| myo-Inositol | 5.55E+00 | 0.00E+00 |
| Glycine | 2.66E−02 | 0.00E+00 |
| Cyanocobalamine | 2.95E−04 | 0.00E+00 |
| Sucrose | 8.76E+01 | 2.92E+01 |

The term "inoculum" as used herein refers to root material prepared from viable root biomass that has been cut into root pieces of about 2 mm to about 30 mm in length, optionally washed with washing medium, and resuspended in fresh growth medium at a concentration of 0.1-2.5 g/L, preferably of 0.5 g/L, dry mass or of 1.5-40 g/L, preferably of 8 g/L wet mass. The inoculum can be used to inoculate, i.e. start, a root organ culture in a bioreactor.

The term "preparing an inoculum" as used herein refers to the process of cutting into pieces of about 2 mm to about 30 mm in length, optionally washing, and resuspending in fresh growth medium at a concentration of 0.1-2.5 g/L, preferably of 0.5 g/L, dry mass or of 1.5-40 g/L, preferably of 8 g/L wet mass viable root material from a viable root biomass.

The term "washing medium" as used herein refers to, e.g., a saline solution, a growth medium, or a buffer solution and is suitable for washing the root material of a root biomass during the process of preparing an inoculum. The term "buffer solution" as used herein is an aqueous solution comprising a mixture of a weak acid and its conjugate base, or vice versa. Buffer solutions are used as a means of keeping the pH at a nearly constant value in a wide variety of conditions and upon addition of a wide variety of substances.

The term "inoculation vessel" as used herein refers to a vessel suitable for preparing an inoculum for a root organ culture therein. The inoculation vessel (see FIG. 1) optionally comprised in the apparatus of the present invention comprises an inoculation chamber (21), a knife (16), wherein the knife (16) is part of a rotatable stirrer blade construction or a knife mill construction, and wherein the knife (16) is located within the inoculation chamber (21), and between three and five outlets, wherein the outlets are for root biomass inlet (15), inoculum outlet (17), aeration, media inlet (18, 19), and media outlet, and wherein the inner diameter is ≥10 mm. Preferably, the inoculation vessel has four outlets, most preferably the inoculation vessel has five outlets. Each outlet is used for as few as possible of root biomass inlet (15), inoculum outlet (17), aeration, media inlet (18, 19), and media outlet; i.e. each outlet is used for two, preferably one, of the above processes only. At least one of the outlets of the inoculation vessel can be fitted with a sterile screw cap or sterile rotary seal. The remaining outlets of the inoculation vessel can be fitted with sterile connectors without flow restrictions. The sterile connectors fitted to the outlets of the inoculation vessel can be connected to tubes. Preferably, the outlet used for inoculum outlet and/or media outlet (17) is located at the bottom of the inoculation vessel, allowing outlet of inoculum and/or media by gravity, application of pressure, or flushing with medium.

The inoculation chamber (21) of the inoculation vessel has a chamber volume of 0.2-50 L, preferably of 0.2-25 L, more preferably of 0.2-10 L, still more preferably of 0.2-5 L, most preferably of 0.2-2 L.

The inoculation vessel is made of glass. More preferably, the inoculation vessel is made of borosilicate glass. Most preferably, the inoculation vessel is made of borosilicate glass 3.3 ("Duran") or "Pyrex". Advantageously, the glass inoculation vessel has high mechanical durability and temperature durability, allowing for sterilization by autoclavation. Furthermore, the glass inoculation vessel is transparent, and any root material of the inoculum remaining in the inoculation vessel after transfer to a bioreactor is clearly visible. Likewise, transparency allows the user to see after how many flushing cycles by recirculating growth medium from the bioreactor through the inoculation vessel all remaining root material has been transferred to the bioreactor.

The knife (16) of the inoculation chamber is part of a rotatable stirrer blade construction or a knife mill construction. Preferably, the knife (16) can be inserted into the inoculation chamber through one of the outlets and is mounted on a sterile rotary seal (20), which can be fitted to the outlet through which the knife (16) is inserted. The knife (16) can be rotated automatically. Preferably, the knife (16) of the rotatable stirrer blade construction rotates with a tip speed of 1-50 m/s. The knife (16) of the inoculation vessel is suitable to cut root material derived from root biomass into root pieces of about 2-30 mm in length inside the inoculation chamber (21) by rotating with a tip speed of 1-50 m/s (if the knife (16) is part of a rotatable stirrer blade construction) or by exerting shear force (if the knife (16) is part of a knife mill construction). The knife (16) of the inoculation vessel is made of metal, preferably of steel, most preferably of austenitic stainless steel, e.g. "WNr. 1.4404 (X2CrNiMo17-12-2), AISI 316L, (A4L)". Advantageously, the metal knife (16) of the invention can be sterilized by autoclavation and has high resistance to corrosion due to chloride in washing or growth media containing chloride.

The screw caps, which can be fitted to at least one of the outlets of the inoculation vessel, are made of polypropylene. The rotary seals, which can be fitted to at least one of the outlets of the inoculation vessel, are made of polytetrafluoroethylene (PTFE). Advantageously, the screw caps and/or rotary seals can be sterilized by autoclavation due to high temperature durability.

The connectors, which can be fitted to the remaining outlets of the inoculation vessel, provide minimal flow restrictions and have a minimum inner diameter of 10 mm. The connectors can be plug junctions. The connectors are made of polycarbonate, polypropylene, or metal, preferably of steel, most preferably of austenitic stainless steel, e.g. "WNr. 1.4404 (X2CrNiMo17-12-2), AISI 316L, (A4L)". Advantageously, the connectors can be sterilized by autoclavation. Exemplary suitable connectors are Kleenpak™ Sterile Connectors (Pall Cooperations, see U.S. Pat. No. 6,655,655 B1) and tri-clamp connectors.

The term "provides minimal flow restrictions" as used herein refers to connectors having a minimal inner diameter of 10 mm, which inner diameter may not change across the length of said connector by more than +/−30%. Furthermore, the inner diameter of the connector must be no less than 70% of the inner diameter of any tubes connected to the connectors.

The term "imposes minimal cross section reduction of the flow path" as used herein refers to connectors having a minimal inner diameter of 10 mm and a free cross section area that may not change across the length of said connector in the direction of flow through the connector by more than −50% and/or +70%.

The tubes which can be connected to the connectors are made of silicone and have a minimum inner diameter of 10 mm. Advantageously, the silicone tubing will not contain leachables, can be autoclaved due to high temperature durability, and have good mechanical stability and elasticity, which is important when connecting them, e.g. to peristaltic pumps.

The term "root biomass inlet" as used herein refers to transferring root material, optionally suspended in growth or washing medium, from a root biomass into the inoculation vessel.

The term "inoculum outlet" as used herein refers to transferring the inoculum prepared inside the inoculation chamber (21) of the inoculation vessel from said inoculation chamber, preferably into a bioreactor.

The terms "aeration" and "gassing" as used herein refer to introducing sterilized air with a composition of 21-30% $O_2$, 0.04-2% $CO_2$, and 68-78.96% $N_2$ into the inoculation vessel and/or bioreactor of the invention. Gassing can be done through the use of a gas sparger. The term "gas sparger" as used herein refers to a device that bubbles sterilized air with a composition of 21-30% $O_2$, 0.04-2% $CO_2$, and 68-78.96% $N_2$ through the medium in the inoculation vessel and/or bioreactor of the invention. Sparging increases the gas-liquid interface. The smaller the bubbles, the gentler the gassing, which is advantageous for preventing damage to the roots of the culture The terms "an outlet", "outlets", "port", and "ports" as used herein refer to an opening in an inoculation vessel or bioreactor, which can be fitted with a connector, a screw cap, or a rotary vacuum seal.

Wherever a port, outlet, tube, connector, plug junction or other component of the inoculation vessel and/or bioreactor has a minimum inner diameter of 10 mm, this is to permit unobstructed flow of root pieces ranging in size from 2-30 mm through that component.

The inoculation vessel can be used in a method of preparing an inoculum as part of a method of producing roots, which is also provided by the invention. The method of preparing an inoculum for a root organ culture from viable root biomass comprises the steps of:

1) introducing root biomass into an inoculation vessel that is part of an apparatus of the invention via one of the three to five outlets in an aseptic environment;
2) cutting the root biomass with the knife (16) of the inoculation vessel;
3) optionally washing the cut root biomass with a washing medium using one or more of the three to five outlet(s) of the inoculation vessel for media inlet and media outlet; and
4) transferring the cut, and optionally washed, inoculum from the inoculation vessel to a bioreactor using one of the three to five outlets for inoculum outlet (17);

wherein steps 2 and 3 are performed inside the inoculation vessel, and wherein steps 2 to 4 do not require an aseptic environment. Therefore, the inventive inoculation vessel and method of preparing an inoculum enable the combination of cutting, optionally washing, and transferring in one vessel that can be scaled to industrial volume requirements without requiring expensive and difficult to scale an aseptic, e.g. clean room, conditions.

Preferably, the root material is cut by rotating the knife (16) of the inoculation vessel with a tip speed of 1-50 m/s if the knife (16) is part of a rotatable stirrer blade construction, or by exerting shear force with the knife (16) of the inoculation vessel if it is part of a knife mill construction. The cutting step is performed at temperatures of 0-35° C. Preferably, the cutting step is performed under cooled conditions, i.e. at temperatures of 0-26° C., to reduce damage to and loss of viability of the root material.

Preferably, the washing medium for washing the root material of the root biomass is saline, growth medium, or a buffer solution. In the washing step, the washing medium is added through one of the outlets of the inoculation vessel, preferably through a dedicated media inlet outlet, to resuspend the root material of the root biomass. The washing medium is then removed through one of the outlets of the inoculation vessel, preferably through an outlet dedicated for medium outlet, which is preferably located at the bottom of the inoculation vessel. The washing medium removal preferably occurs through pouring, pumping, gravitation, or applying overpressure, most preferably through pumping.

The transfer step occurs through a sterile connector, which provides minimal flow restrictions and/or does not impose cross section reduction of the flow path and has a minimum inner diameter of 10 mm.

The inoculum prepared by the above inventive method contains root pieces of 2 mm to about 30 mm in length at a concentration of 0.1-2.5 g/L, preferably of 0.5 g/L, dry mass or of 1.5-40 g/L, preferably of 8 g/L wet mass suspended in growth medium.

The term "bioreactor" as used herein refers to a vessel suitable for cultivating a root organ culture therein. The bioreactor of the present invention (see FIG. 2) comprises a cultivation chamber (2); a fast rotatable knife or a rotor stator (6) located at the bottom of the bioreactor; an inoculation port (1), wherein the inner diameter of the inoculation port is 10 mm; a harvest port (5), wherein the inner diameter of the harvest port is ≥10 mm and wherein the harvest port is located at the bottom of the bioreactor; and two aeration outlets (3, 4), wherein one aeration outlet is for gas inlet and the other aeration outlet is for gas outlet.

The bioreactor further optionally comprises a gas sparger (7), wherein the aeration outlet for gas inlet is connected to a gas sparger. Optionally, the bioreactor comprises a second gas sparger and alternatively or further comprises one to four outlets for dip tubes (8), wherein the one to four dip tubes are for base addition, feed addition, acid addition, and/or sampling. Optionally, the bioreactor alternatively or further comprises one to three ports for probes (9), wherein the probes are for measuring pH, dissolved oxygen, and/or conductivity.

The bioreactor of the invention, including all fittings, covers, ports, and outlets, is made of metal, preferably of steel, most preferably of austenitic stainless steel, e.g. "WNr. 1.4404 (X2CrNiMo17-12-2), AISI 316L, (A4L)". Advantageously, the bioreactor of the invention can be sterilized by autoclavation and has high resistance to corrosion due to chloride in washing or growth media containing chloride.

The cultivation chamber (2) is a chamber within the bioreactor in which the culturing step is performed. The cultivation chamber (2) volume is from 1-100000 L, preferably from 10-100000 L, more preferably from 1000-100000 L, most preferably from 10000-100000 L.

The fast rotatable knife (6) of the bioreactor is located at the bottom of the bioreactor, can be rotated at a tip speed of 1-50 m/s, and is made of metal, preferably of steel, most preferably of austenitic stainless steel, e.g. "WNr. 1.4404 (X2CrNiMo17-12-2), AISI 316L, (A4L)". Advantageously, the fast rotatable knife (6) of the invention can be sterilized by autoclavation and has high resistance to corrosion due to chloride in washing or growth media.

The rotor stator (6) of the bioreactor is located at the bottom of the bioreactor and is made of metal, preferably of steel, most preferably of austenitic stainless steel, e.g. "WNr. 1.4404 (X2CrNiMo17-12-2), AISI 316L, (A4L)". Advantageously, the rotor stator (6) of the invention can be sterilized by autoclavation and has high resistance to corrosion due to chloride in washing or growth media containing chloride.

The inoculation port (1) is preferably located in the upper half of the inoculation vessel and can be connected to a sterile connector, which imposes minimal flow restrictions and/or imposes minimal reductions of the cross section, and which in turn can be connected to a tube or pipe leading to an inoculation vessel. A root inoculum is transferred through this port (1) into the cultivation chamber (2) of the bioreactor to start a root organ culture. The inoculation port (1) has a minimum inner diameter of 10 mm.

The harvest port (5) is located at the bottom of the inoculation vessel, which permits the harvest of root material cut to a size of 2-30 mm and suspended in growth medium by gravity, and has a minimum inner diameter of 10 mm.

The gas sparger (7) may be any of the following types: sparging tube, sintered stainless steel sparger, porous stainless steel element, spider type sparger, ring sparger. The gas sparger (7) is used to gas the root organ culture inside the cultivation chamber (2) of the bioreactor. The gas sparger (7) is made of metal, preferably of steel, most preferably of austenitic stainless steel, e.g. "WNr. 1.4404 (X2CrNiMo17-12-2), AISI 316L, (A4L)". Advantageously, the gas sparger (7) of the invention can be sterilized by autoclavation and has high resistance to corrosion due to chloride in washing or growth media containing chloride.

The terms "aeration" and "gassing" as used herein refer to pumping sterilized air with a composition of 21-30% $O_2$, 0.04-2% $CO_2$, and 68-78.96% $N_2$ into and/or out of the inoculation vessel and/or bioreactor of the invention.

Wherever a port, outlet, tube, connector, plug junction or other component of the inoculation vessel and/or bioreactor has a minimum inner diameter of 10 mm, this is to permit unobstructed flow of root pieces ranging in size from 2-30 mm through that component.

The term "dip tube" as used herein refers to a tube, which can be submerged in the root organ culture within the cultivation chamber (2) of the bioreactor. They can be used, e.g., for the addition of bases or acids to adjust culture pH and/or to dissolve a polysaccharide attachment matrix, for the addition of fresh medium ("feed") in a fed batch culture, and/or for taking samples of the root organ culture during cultivation.

The bioreactor of the invention can also be used in a method of producing and aseptically harvesting roots of the invention. The method of producing and aseptically harvesting roots comprises the steps of:
1) cultivating a root organ culture in a growth medium inside a bioreactor of the invention;
2) optionally detaching the roots of the root organ culture from the attachment matrix (9a, 9b, or 9c) inside the bioreactor;
3) letting the roots settle;
4) cutting the settled roots inside the bioreactor using the fast rotatable knife or the rotor stator (6) at the bottom of the bioreactor; and
5) removing the cut roots using the harvest port (5);

wherein steps 1-4 are performed inside the bioreactor and wherein steps 1-5 do not require an aseptic environment. Therefore, the inventive bioreactor and method of producing and aseptically harvesting root material enable the combination of cultivating, optionally detaching, cutting and removing root material in one vessel that can be scaled to industrial volume requirements without requiring expensive and difficult to scale aseptic, e.g. clean room, conditions.

The cultivating step is preferably performed for 1-12 weeks, and can be done as submersion culture, e.g. as batch culture, fed batch culture, or batch culture followed by fed batch culture, or as trickle-bed culture. In one embodiment, the culture is a submersion culture that is a batch culture for 3-4 weeks followed by 8 weeks of fed batch culture.

Figure 3:
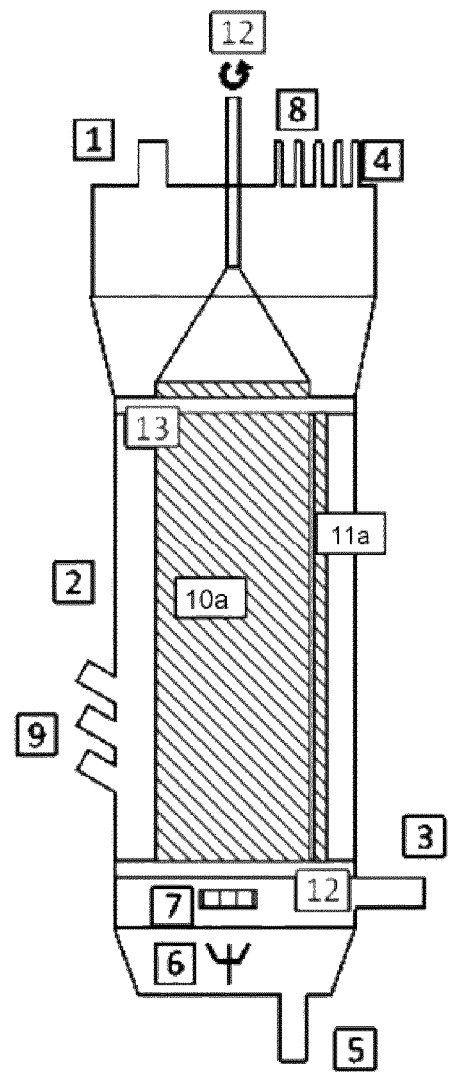
FIG. 3 shows a bioreactor for producing and aseptically harvesting roots, comprising an inoculation port (1), a cultivation chamber (2), two aeration outlets (3, 4), a harvest port (5), a fast rotatable knife (6), a gas sparger (7), four outlets for dip tubes (8), three ports for probes (9), a rotatable attachment matrix (10a), a vertical shearing knife (11a), a rotatable attachment matrix mounting (12), and a support ring for the shearing blade (13).

In one embodiment (see FIG. 3), the bioreactor further comprises an attachment matrix (10a), a rotatable attachment matrix mounting (12), a vertical shearing blade (11b) for root detachment, and a support ring for the shearing blade (13), wherein the attachment points on the attachment matrix (10a) are vertically arranged, and wherein the attachment matrix (10a) is vertically rotatable on the rotatable attachment matrix mounting (12), and wherein the vertical shearing blade (11b) is static. The attachment matrix (10a) is made of metal, preferably of steel, most preferably of austenitic stainless steel, e.g. "WNr. 1.4404 (X2CrNiMo17-12-2), AISI 316L, (A4L)". Advantageously, the attachment matrix (10a) of the invention can be sterilized by autoclavation and has high resistance to corrosion due to chloride in washing or growth media containing chloride. The attachment matrix (10a) can be made from a perforated sheet of metal or from a metal grid, where holes in the sheet or grid serve as attachment points for the roots of the culture. Preferably, the attachment matrix (10a) is a mesh. More preferably, the mesh size is from 2×2 mm to 50×50 mm, e.g. 2×2 mm, 3×3 mm, 4×4 mm, 5×5 mm, 6×6 mm, 7×7 mm, 8×8 mm, 9×9 mm, 10×10 mm, 11×11 mm, 12×12 mm, 13×13 mm, 14×14 mm, 15×15 mm, 16×16 mm, 17×17 mm, 18×18 mm, 19×19 mm, 20×20 mm, 21×21 mm, 22×22 mm, 23×23 mm, 24×24 mm, 25×25 mm, 26×26 mm, 27×27 mm, 28×28 mm, 29×29 mm, 30×30 mm, 31×31 mm, 32×32 mm, 33×33 mm, 34×34 mm, 35×35 mm, 36×36 mm, 37×37 mm, 38×38 mm, 39×39 mm, 40×40 mm, 41×41 mm, 42×42 mm, 43×43 mm, 44×44 mm, 45×45 mm, 46×46 mm, 47×47 mm, 48×48 mm, 49×49 mm, or 50×50 mm. The most preferred mesh size will depend on the average size of the root fragments with which the culture is inoculated. The vertical shearing blade (11a) is made of metal, preferably of steel, most preferably of austenitic stainless steel, e.g. "WNr. 1.4404 (X2CrNiMo17-12-2), AISI 316L, (A4L)". Advantageously, the vertical shearing blade (11a) of the invention can be sterilized by autoclavation and has high resistance to corrosion due to chloride in washing or growth media containing chloride. When using the bioreactor of this embodiment, the method of producing and aseptically harvesting roots comprises detachment of the roots by the use of shear force exerted by the shearing blade (11a) on the rotating matrix (10a). Specifically, in the bioreactor of this embodiment, root material of the inoculum will attach to the attachment points of the attachment matrix (10a) and begin to grow during the cultivation period. Once a suitable density of root material has been reached in the culture, the attachment matrix (10a) can then be rotated and the static shearing knife (11a) will cut loose the root material by exerting shear force across the surface of the rotating attachment matrix (10a). Both the roots growing toward the center of the cultivation chamber (2) and the roots growing toward the outside of the cultivation chamber (2) will thus be detached and settle through gravity at the bottom of the bioreactor.

Figure 2:
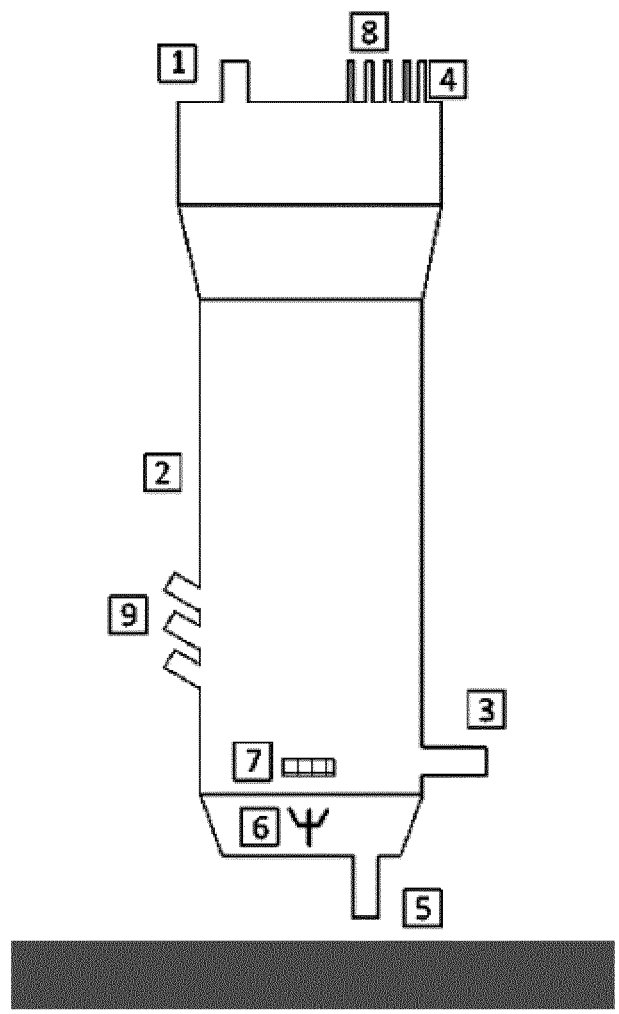
FIG. 2 shows a bioreactor for producing and aseptically harvesting roots, comprising an inoculation port (1), a cultivation chamber (2), two aeration outlets (3, 4), a harvest port (5), a fast rotatable knife (6), a gas sparger (7), four outlets for dip tubes (8), and three ports for probes (9).

In another embodiment, the bioreactor does not comprise an attachment matrix (see FIG. 2). When using the bioreactor of this embodiment, the method of producing and aseptically harvesting roots comprises inducing continuous culture medium movement by gassing the root organ culture at 0.2-50 sL/L/h throughout the cultivation step through the use of the gas sparger (7). The gassing is done with sterilized air with a composition of 21-30% $O_2$, 0.04-2% $CO_2$, and 68-78.96% $N_2$. Specifically, the roots will grow freely in suspension, with the culture medium movement preventing settling and/or rising as well as formation of excessive clumping. Once a suitable density of root material has been reached in the culture, gassing is ceased, and the root material will settle through gravity at the bottom of the bioreactor.

Figure 4:
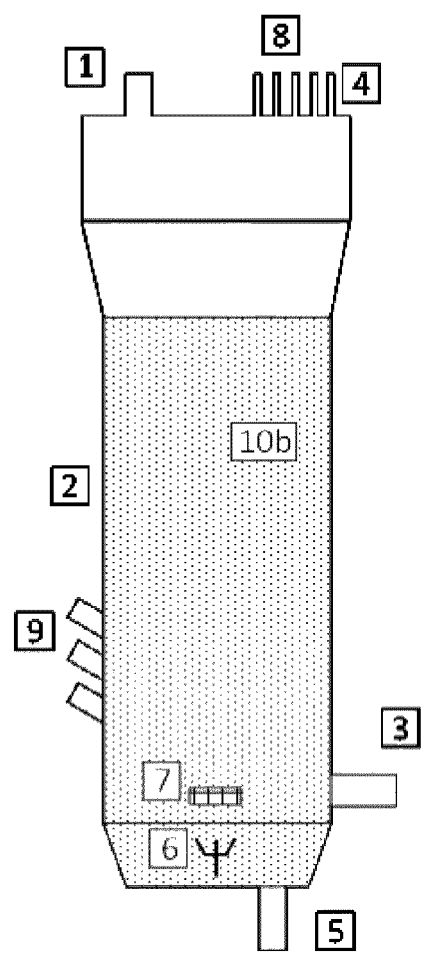
FIG. 4 shows a bioreactor for producing and aseptically harvesting roots, comprising an inoculation port (1), a cultivation chamber (2), two aeration outlets (3, 4), a harvest port (5), a fast rotatable knife (6), a gas sparger (7), four outlets for dip tubes (8), three ports for probes (9), and an attachment matrix composed of beads (10b).

In yet another embodiment, the bioreactor further comprises an attachment matrix (10b), wherein the attachment matrix (10b) is composed of beads, said beads comprising a polysaccharide and a growth medium. (see FIG. 4). Preferably, the polysaccharide is selected from the group consisting of alginate, agarose, and gellan. Preferably, the beads have a diameter of 1-5 mm. When using the bioreactor of this embodiment, the method of producing and aseptically harvesting roots comprises inducing continuous culture medium movement by gassing the root organ culture at 0.2-50 sL/L/h throughout the cultivation step through the use of the gas sparger (7), and the detachment step comprises dissolving the attachment matrix (10b) beads. The gassing is done with sterilized air with a composition of 21-30% $O_2$, 0.04-2% $CO_2$, and 68-78.96% $N_2$. The dissolving of the attachment matrix (10b) beads is done by addition of citric acid, preferably 10 mM citric acid with a pH of 5-6, or of a polysaccharide cleaving enzyme. The polysaccharide cleaving enzyme will depend on the polysaccharide used. For alginate beads, alginate lyase is added; for gellan beads, gellan lyase is added; and for agarose, beta-agarase is added. Specifically, the roots of the inoculum will attach to the attachment matrix (10b) beads, which float freely in suspension due to gassing-induced culture medium movement in the growth medium. The roots then grow, and eventually form inter-bead clumps. Once a suitable density of root material has been reached in the culture, gassing is ceased and the beads sink to the bottom of the bioreactor through gravity. By dissolving of the beads, only root material remains settled at the bottom of the bioreactor.

Figure 5:
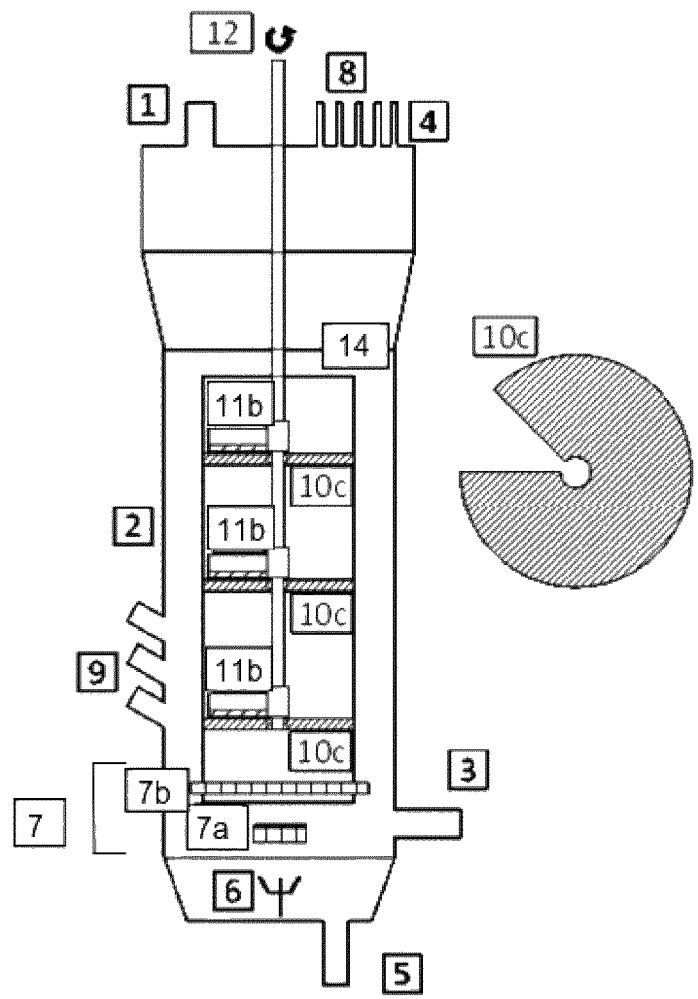
FIG. 5 shows a bioreactor for producing and aseptically harvesting roots, comprising an inoculation port (1), a cultivation chamber (2), two aeration outlets (3, 4), a harvest port (5), a fast rotatable knife (6), a gas sparger (7) consisting of two independently usable sparging elements, one of which (7a) is located beneath the center of the draft tube and the other one of which (7b) is a ring sparger located outside of the draft tube in the lower half of the cultivation chamber, four outlets for dip tubes (8), three ports for probes (9), an attachment matrix composed of horizontal root support disks (10c), horizontally arranged detachment knives (11a), a central, vertical rotary shaft (12), and a cylindrical draft tube (14).

In yet another embodiment, the bioreactor (see FIG. 5) further comprises an attachment matrix (10c), a central, vertical rotary shaft; and multiple horizontally arranged detachment knives (11b); wherein the attachment matrix (10c) is composed of multiple, horizontal root support disks, and wherein said root support disks are spaced in regular distances of ≥7 cm, and wherein the detachment knives (11b) are mounted horizontally on the vertical rotary shaft so that one detachment knife (11b) is located at a distance of 0.05-5 mm from each root support disk, and wherein the number of detachment knives (11b) is the same as or larger than the number or root support disks. In an embodiment, the root support disks have an area of circle sectors of 30-360°, preferably of 45-320°, more preferably of 60-270°. The larger the open section of the root support disks, the better media can circulate around and between the root support disks. The height of the detachment knives (11b) is up to 10%, up to 20%, up to 30%, up to 40%, up to 50%, up to 60%, up to 70%, up to 80%, up to 90%, or up to 100% of the distance between neighboring root support disks. Preferably, the height of the detachment knives (11b) is up to 100% of the distance between neighboring root support disks. The central vertical rotary shaft, the detachment knives (11b) and the root support disks of the attachment matrix (10c) are made of metal, preferably of steel, most preferably of austenitic stainless steel, e.g. "WNr. 1.4404 (X2CrNiMo17-12-2), AISI 316L, (A4L)". Advantageously, these components of the invention can be sterilized by autoclavation and have high resistance to corrosion due to chloride in washing or growth media containing chloride. The multiple root disks are lattices or stainless steel perforated plates, with the holes in the lattices and/or plates serving as attachment points for the roots of the culture. Preferably, the multiple root support disks are meshes. More preferably, the mesh size is from 2×2 mm to 50×50 mm, e.g. 2×2 mm, 3×3 mm, 4×4 mm, 5×5 mm, 6×6 mm, 7×7 mm, 8×8 mm, 9×9 mm, 10×10 mm, 11×11 mm, 12×12 mm, 13×13 mm, 14×14 mm, 15×15 mm, 16×16 mm, 17×17 mm, 18×18 mm, 19×19 mm, 20×20 mm, 21×21 mm, 22×22 mm, 23×23 mm, 24×24 mm, 25×25 mm, 26×26 mm, 27×27 mm, 28×28 mm, 29×29 mm, 30×30 mm, 31×31 mm, 32×32 mm, 33×33 mm, 34×34 mm, 35×35 mm, 36×36 mm, 37×37 mm, 38×38 mm, 39×39 mm, 40×40 mm, 41×41 mm, 42×42 mm, 43×43 mm, 44×44 mm, 45×45 mm, 46×46 mm, 47×47 mm, 48×48 mm, 49×49 mm, or 50×50 mm. The most preferred mesh size will depend on the average size of the root fragments with which the culture is inoculated. When using the bioreactor of this embodiment, the detaching step of the method of producing and aseptically harvesting roots is accomplished by the use of shear force exerted by the detachment blades (11b) rotating above the root support disks. Specifically, the roots of the inoculum will attach at the attachment points of the root support disks of the attachment matrix (10c) and begin to grow during the cultivating step. Once a suitable density of root material has been reached in the culture, the detachment knives (11b) are rotated, and shear the roots growing on top of the root support disks off. If the height of the detachment knives (11b) approaches or is 100% of the distance between neighboring root support disks, the rotating detachment knives will also shear off the roots growing below the next higher support disk. The detached roots, both from above and below the root support disks, then settle through gravity at the bottom of the bioreactor. When using the bioreactor of this embodiment, the method of producing and aseptically harvesting roots may comprise inducing continuous culture medium movement by gassing the root organ culture at 0.2-50 sL/L/h throughout the cultivation step through the use of the gas sparger (7). The gassing is done with sterilized air with a composition of 21-30% $O_2$, 0.04-2% $CO_2$, and 68-78.96% $N_2$.

In a preferred embodiment, the bioreactor (see FIG. 5) of the above embodiment may further comprise a cylindrical draft tube (14), wherein the horizontal root support disks are mounted inside of the cylindrical draft tube (14). The draft tube consists of a cylinder, which is fully open at its top and bottom end. The draft tube (14) is made of metal, preferably of steel, most preferably of austenitic stainless steel, e.g. "WNr. 1.4404 (X2CrNiMo17-12-2), AISI 316L, (A4L)". Advantageously, the draft tube (14) of the invention can be sterilized by autoclavation and has high resistance to corrosion due to chloride in washing or growth media containing chloride. If the root organ culture is a submersion culture, preferably, the draft tube is entirely submerged in the culture medium during culturing to improve uniformity of distribution of the biomass in the culture and to increase the percentage of total biomass that is harvestable. In this embodiment, the gas sparger (7) consists of two independently usable sparging elements, one of which (7a) is located beneath the center of the draft tube and the other one of which (7b) is a ring sparger located either below or outside the draft tube in the lower half of the cultivation chamber. When using the bioreactor of this embodiment, the method of producing and aseptically harvesting roots comprises inducing continuous medium movement by gassing the root organ culture at 0.2-50 sL/L/h throughout the cultivation step through the use of the gas sparger (7a). The gassing is done with sterilized air with a composition of 21-30% $O_2$, 0.04-2% $CO_2$, and 68-78.96% $N_2$.

In all of the bioreactors and methods of producing and aseptically harvesting roots of the invention, the cutting step is accomplished by rotating the fast rotatable knife (6) at a top speed of 1-50 m/s or by running the rotor stator (6) once the roots of the culture have settled at the bottom of the bioreactor. The cutting step is performed at temperatures of 0-35° C. Preferably, the cutting step is performed under cooled conditions, i.e. at temperatures of 0-20° C., to reduce damage to and loss of viability of the root material. The cut roots pieces to be harvested will have a size of 2-30 mm.

In all of the bioreactors and methods of producing and aseptically harvesting roots of the invention, the removing step is accomplished using a peristaltic pump or a screw conveyor or by flushing with growth medium.

The invention further provides an apparatus for inoculation, cultivation, and harvest of root organ cultures, comprising a first bioreactor of the invention, and at least one further bioreactor of the invention, wherein said first bioreactor is connected to said at least one further bioreactor. This apparatus may be, e.g., a seed train.

The above apparatus of the invention can be used in a method of producing roots, comprising a method of preparing an inoculum for a root organ culture from viable root biomass, comprising the following steps:
1) introducing viable root biomass into the a first bioreactor of the apparatus via the inoculation port (1) in an aseptic environment;
2) optionally cultivating the introduced root biomass in the presence of a growth medium
3) optionally cutting the root biomass with the fast rotatable knife or rotor stator (6) of the first bioreacor, optionally wherein the cutting step is performed at a temperature of 0-35° C.,
4) transferring the cut inoculum from the first bioreactor to the at least one further bioreactor using the harvest port (5) of the first bioreactor and the inoculation port (1) of the at least one further bioreactor,
optionally wherein the transfer step occurs through a sterile connector, wherein the sterile connector provides minimal flow restrictions and/or wherein the connector imposes minimal cross section reduction of the flow path, optionally wherein the method further comprises a step of flushing the first bioreactor by recirculating growth medium from the at least one further bioreactor to the first bioreactor
wherein steps 2 and 3 are performed inside the first bioreactor, and wherein steps 2 to 4 do not require an aseptic environment;
followed by the method of producing and aseptically harvesting roots of the invention;
wherein the first bioreactor and the at least one further bioreactor are comprised in the above apparatus.

Finally, the invention also provides an apparatus that comprises both an inoculation vessel as described above and a bioreactor of the invention, which are connected. The connection can comprise a sterile connector fitted to one of the three to five outlets of the inoculation vessel, a sterile connector fitted to the inoculation port (15) of the bioreactor, and a tube or pipe attached to these sterile connectors, wherein the sterile connectors, tube and/or pipe impose minimal flow restrictions and/or impose minimal cross section reduction of the flow path and have a minimum inner diameter of 10 mm. The sterile connectors and pipe are made of metal, preferably of steel, most preferably of austenitic stainless steel, e.g. "WNr. 1.4404 (X2CrNiMo17-12-2), AISI 316L, (A4L)". Advantageously, the sterile connectors and pipe of the apparatus can be sterilized by autoclavation and have high resistance to corrosion due to chloride in washing or growth media containing chloride. The tube is made of silicone and has a minimum inner diameter of 10 mm. Advantageously, the silicone tubing will not contain leachables, can be autoclaved due to high temperature durability, and have good mechanical stability and elasticity, which is important when connecting them, e.g., to peristaltic pumps.

The above apparatus of the invention can be used in a method of producing hairy roots, which comprises a method of preparing an inoculum as described above followed by a method of producing and aseptically harvesting roots of the invention.

The invention further provides the following embodiments:
1. Inoculation vessel for preparing an inoculum for a hairy root culture from viable hairy root biomass, comprising:
    an inoculation chamber (21);
    a knife (16), wherein the knife (16) is part of a rotatable stirrer blade construction or a knife mill construction and wherein the knife (16) is located within the chamber;
    between three and five outlets from the chamber, wherein the outlets are for hairy root biomass inlet (15), inoculum outlet (17), aeration, media inlet, and media outlet, and wherein the inner diameter of the outlets is ≥10 mm.
2. The inoculation vessel of embodiment 1, wherein the between three and five outlets are used for as few of hairy root biomass inlet (15), inoculum outlet (17), aeration, media inlet, and media outlet as possible.
3. The inoculation vessel of embodiment 1 or 2, wherein at least one of the three to five outlets can be fitted with a sterile screw cap or sterile rotary seal, and wherein the remaining outlets can be fitted with sterile connectors without flow restrictions, and wherein the sterile connector can be connected to tubes.
4. The inoculation vessel of any one of the preceding embodiments, wherein the outlet for inoculum outlet and/or media outlet (17) is located at the bottom of the inoculation vessel.
5. The inoculation vessel of any one of the preceding embodiment, wherein the inoculation chamber (17) volume is 0.2-50 L, preferably 0.2-2 L.
6. Method of preparing an inoculum for a hairy root culture from viable hairy root biomass, comprising the following steps:
   1) introducing viable hairy root biomass into the inoculation vessel of any one of embodiment s 1-5 via one of the three to five outlets in an aseptic environment;
   2) cutting the hairy root biomass with the knife (16) of the inoculation vessel;
   3) optionally washing the cut hairy root biomass with a washing medium using one or more of the three to five outlet(s) of the inoculation vessel for media inlet and media outlet; and
   4) transferring the cut, optionally washed, inoculum from the inoculation vessel to a bioreactor using one of the three to five outlets (17) for inoculum outlet;
   wherein steps 2 and 3 are performed inside the inoculation vessel, and wherein steps 2 to 4 do not require an aseptic environment.
7. The method of embodiment 6, wherein the cutting is performed by
   rotating the knife (16) of the rotatable stirrer blade construction with a tip speed of 1-50 m/s, or
   rotating the knife (16) of the knife mill construction to exert shear force.
8. The method of embodiment 6 or 7, wherein the cutting step is performed at a temperature of 0-20° C.
9. The method of any one of embodiments 6-8, wherein the washing medium is selected from the group of a saline solution, a growth medium, and a buffer solution.
10. The method of any one of embodiments 6-9, wherein the washing medium is added to the inoculation vessel to resuspend the cut hairy root biomass via one of the three to five outlets and wherein the washing medium is removed from the inoculation medium via one of the three to five outlets.
11. The method of embodiment 10, wherein the removal of the washing medium occurs via pouring, pumping, gravitation, or applying overpressure.
12. The method of any one of embodiments 6-11, wherein the transfer step occurs through a sterile connector, wherein the sterile connector provides minimal flow restrictions and/or wherein the connector imposes minimal cross section reduction of the flow path.
13. The method of any one of embodiments 6-12, wherein the method further comprises a step of flushing the inoculation vessel by recirculating growth medium from the bioreactor to the inoculation vessel.
14. Bioreactor for the cultivation of hairy root cultures, comprising:
   a cultivation chamber (2);
   a fast rotatable knife or a rotor stator (6) located at the bottom of the bioreactor;
   an inoculation port (1), wherein the inner diameter of the inoculation port (1) is ≥10 mm;
   a harvest port (5), wherein the inner diameter of the harvest port (5) is ≥10 mm and wherein the harvest port (5) is located at the bottom of the bioreactor; and
   two aeration outlets (3, 4), wherein one aeration outlet is for gas inlet and the other aeration outlet is for gas outlet.
15. The bioreactor of embodiment 14, further comprising one to four outlets for dip tubes (8), wherein the one to four dip tubes are for base addition, feed addition, acid addition, and/or sampling.
16. The bioreactor of embodiment 14 or 15, further comprising one to three ports for probes (9), wherein the probes are for measuring pH, dissolved oxygen, and/or conductivity.
17. The bioreactor of any one of embodiments 14-16, wherein the cultivation chamber (2) volume is from 1-100000 L.
18. The bioreactor of any one of embodiments 14-17, further comprising
   an attachment matrix (10*a*);
   a rotatable attachment matrix mounting (12);
   a vertical shearing blade (11*a*) for root detachment; and
   a support ring for the shearing blade (13);
   wherein the attachment points on the attachment matrix (10*a*) are vertically arranged, and wherein the attachment matrix (10*a*) is vertically rotatable on the rotatable attachment matrix mounting (12) and the vertical shearing blade (11*a*) is static.
19. The bioreactor of any one of embodiments 14-17, wherein the bioreactor does not comprise an attachment matrix.
20. The bioreactor of any one of embodiments 14-17, further comprising
   an attachment matrix (10*b*),
   wherein the attachment matrix (10*b*) is composed of beads, said beads comprising a polysaccharide and a growth medium.
21. The bioreactor of embodiment 20, wherein the polysaccharide is selected from the group consisting of alginate, agarose, and gellan.
22. The bioreactor of embodiment 20 or 21, wherein the beads have a diameter of 1-5 mm.
23. The bioreactor any one of embodiments 14-17, further comprising
   an attachment matrix (10*c*);
   a central, vertical rotary shaft; and
   multiple horizontally arranged detachment knives (11*b*);
   wherein the attachment matrix (10*c*) is composed of multiple, horizontal root support disks, and wherein said root support disks are spaced in regular distances of ≥10 cm, and wherein the detachment knives (11*b*) are mounted horizontally on the vertical rotary shaft so that one detachment knife (11*b*) is located at a distance of 0.05-5 mm from each root support disk, and wherein the number of detachment knives (11*b*) is the same as the number or root support disks.
24. The bioreactor of embodiment 23, wherein the multiple root disks are stainless steel lattices or stainless steel perforated plates.
25. The bioreactor of claim 23 or 24, further comprising
   a cylindrical draft tube (14)
   wherein the horizontal root support disks are mounted inside of the cylindrical draft tube (14), wherein the cylindrical draft tube (14) consists of a cylinder that is fully open at its top and bottom ends, and wherein the gas sparger (7) consists of one, sparging element, optionally of two independently usable sparging elements, one of which (7*a*) is located beneath the center of the draft tube and the other one of which (7*b*) is a ring sparger located outside and above the bottom opening of the draft tube.

26. Method of producing and aseptically harvesting hairy roots, comprising the steps of
   1) cultivating a hairy root culture in a growth medium inside the bioreactor of any one of embodiments 14-25;
   2) optionally detaching the hairy roots of the hairy root culture from the attachment matrix inside the bioreactor;
   3) letting the hairy roots settle;
   4) cutting the settled hairy roots inside the bioreactor using the fast rotatable knife or the rotor stator (6) at the bottom of the bioreactor; and
   5) removing the cut hairy roots using the harvest port (5); wherein steps 1-4 are performed inside the bioreactor and wherein steps 1-5 do not require an aseptic environment.
27. The method of embodiment 26, wherein the cultivating step is performed for 1-12 weeks.
28. The method of embodiment 26, wherein the bioreactor is the bioreactor of embodiment 18 and wherein the detaching step is accomplished by the use of shear force exerted by the shearing blade (11*a*) on the rotating matrix.
29. The method of embodiment 26, wherein the bioreactor is the bioreactor of any one of embodiments 19-22, wherein the cultivating step comprises inducing turbulence by gassing the hairy root culture at 0.2-50 sL/L/h throughout the step of cultivating.
30. The method of embodiment 29, wherein the gassing is done with sterile air with a composition of 21-30% $O_2$, 0.04-2% $CO_2$, and 68-78.96% $N_2$.
31. The method of embodiment 26, wherein the bioreactor is the bioreactor of any one of embodiments 20-22, and wherein the detaching step is accomplished by dissolving the attachment matrix (10*b*) beads.
32. The method of embodiment 31, wherein the attachment matrix (10*b*) beads are dissolved by addition of citric acid or a polysaccharide cleaving enzyme.
33. The method of embodiment 32, wherein the citric acid is 10 mM citric acid with a pH of 5-6.
34. The method of embodiment 33, wherein the polysaccharide cleaving enzyme is selected from the group consisting of alginate lyase, gellan lyase, and beta-agarase.
35. The method of embodiment 26, wherein the bioreactor is the bioreactor of any one of embodiments 23 to 25, wherein the detaching step is accomplished by the use of shear force exerted by the detachment blades (11*b*) rotating above the root support disks.
36. The method of any one of embodiments 26-35, wherein the cutting step is accomplished by rotating the fast rotatable knife (6) at a tip speed of 1-50 m/s or the rotor stator (6) at the bottom of the bioreactor.
37. The method of any one of embodiments 26-36, wherein the cutting step is performed at a temperature of 0-20° C.
38. The method of any one of embodiments 26-37, wherein the removing step is accomplished using a peristaltic pump or a screw conveyor or by flushing with growth medium.
39. Apparatus for inoculation, cultivation, and harvest of hairy root cultures, comprising the inoculation vessel of any one of embodiments 1-5 and the bioreactor of any one of embodiments 14-25, wherein said inoculation vessel is connected to said bioreactor.
40. Method of producing hairy roots, comprising the method of preparing an inoculum of any one of embodiments 6-13 followed by the method of producing and aseptically harvesting of any one of embodiments 26-38, and wherein the inoculation vessel and bioreactor are comprised in the apparatus of embodiment 39.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

The detailed description is merely exemplary in nature and is not intended to limit application and uses. The following examples further illustrate the present invention without, however, limiting the scope of the invention thereto. Various changes and modifications can be made by those skilled in the art on the basis of the description of the invention, and such changes and modifications are also included in the present invention.

Examples

1. Laboratory Scale Hairy or Adventitious Root Inoculum Preparation

Figure 6:
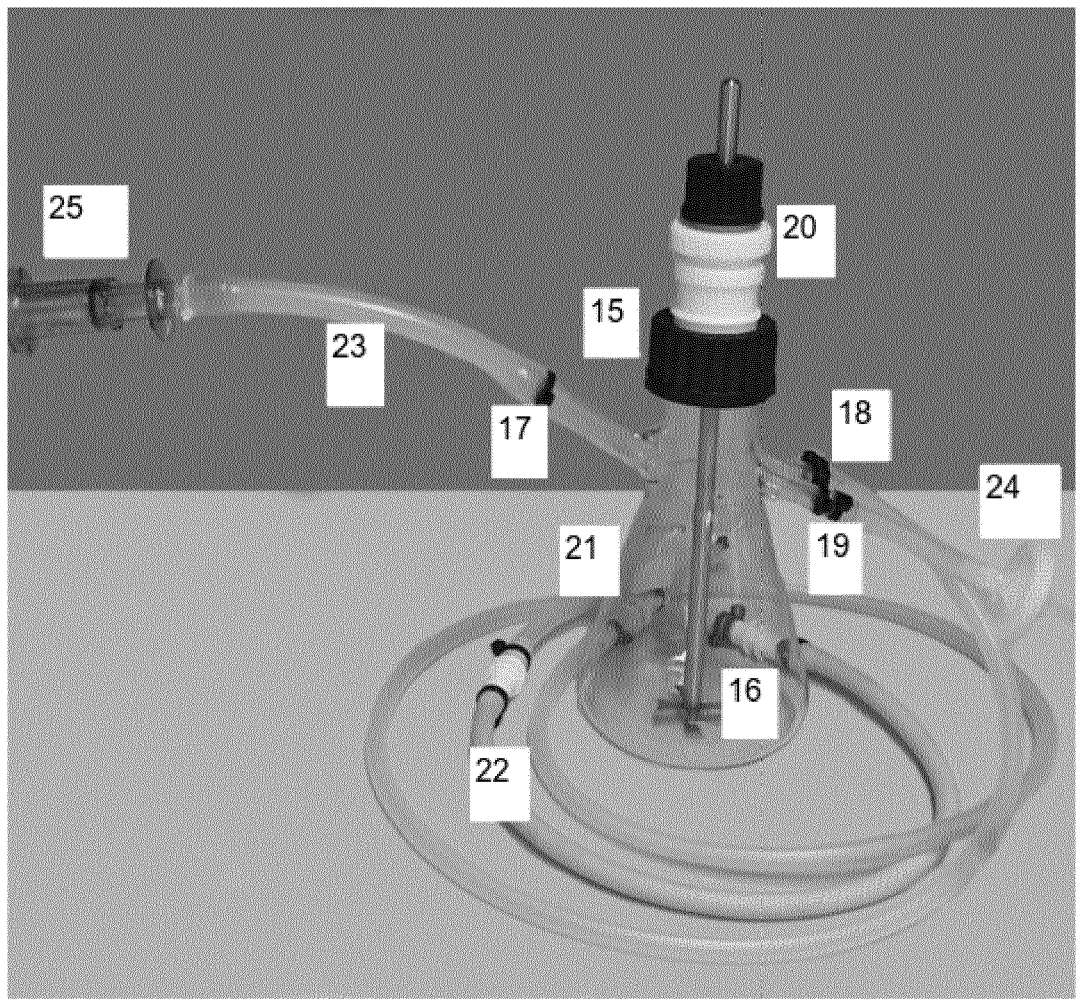
FIG. 6 shows a lab scale inoculation vessel prototype for preparing a 3 L root inoculum from viable root biomass, comprising a root biomass inlet (15), a knife (16), outlets for inoculum outlet (17), medium inlet, medium outlet (19), and aeration (18), a rotary seal mount (20) for the knife, an inoculation chamber (21), an media transfer tube (22), an outlet tube (23) connected to the bioreactor to be inoculated via a sterile connector (25) without any flow path restrictions, and a sterile filter (24).

FIG. 6 shows a lab scale inoculation vessel prototype for preparing a 3 L hairy or adventitious root inoculum and bioreactor inoculation with the inoculum by using one vessel for the combined process steps of cutting, optionally washing, and transferring the hairy or adventitious root inoculum.

The uncut hairy or adventitious root culture is transferred into the inoculation vessel via a top end opening (15). The inoculation vessel is then equipped with a top mounted rotary seal (20) which serves as the bearing for a stirrer shaft for a rotatable knife (16). Medium, saline solution, or sterile water can be added to the flask via the media inlet port (18) using a rotary pump and the media transfer tube (22). For the purpose of washing, an outlet tube (23) can be used for decanting the medium and resuspending the hairy or adventitious roots with fresh media through the media inlet port (18). A sterile filter (24) serves the purpose of sterile pressure compensation in order to avoid overpressure caused by pumping media into the flask. After cutting and washing of the hairy or adventitious root material, the outlet tube (23) connected to the inoculum outlet (17) is further connected to a bioreactor to be inoculated via a sterile connector (25) imposing minimal flow path restrictions. The bioreactor inoculation port must therefore be equipped with the same type of sterile connector. For inoculation, the cut and washed inoculum suspended in media is transferred into the reactor using gravity. For ease of handling, pressurized air can be supplied via the sterile filter (24). The vessel can be refilled with fresh media from the reactor, pumped into the vessel via the media inlet port (18), for the purpose of resuspending and flushing remaining hairy or adventitious root pieces. The transfer is usually completed after 2-4 refill/flushing cycles.

In detail, the inoculation vessel is loaded under laminar flow by sterilizing forceps over their whole length using a Bunsen burner and transferring a hairy or adventitious root pre-culture from a pre-culture shake flask into the inoculation vessel using the top opening (15) with the sterile forceps. Next, the stirrer shaft/rotatable knife bearing (16) is assembled and inserted into the top mounted rotary seal (20) is tested for a tight fit. Laminar flow or other aseptic environments are now no longer required. Homogenization is achieved by equipping the inoculation vessel with the stirrer shaft and drive and rotating the rotatable knife (16) at 2500 rpm for 30 seconds. For washing of the culture with fresh washing medium, fresh, autoclaved washing medium is pumped into the inoculation vessel using the media transfer tube (22) and a peristaltic pump. The hairy or adventitious roots are then decanted by pouring the washing medium out of the inoculation vessel using the inoculum outlet (17) connected to the outlet tube (23). The outlet tube (23) is then capped with sterile aluminum foil. For transfer of the culture, the media transfer tube (22) is attached to a bioreactor and mounted on a peristaltic pump. Next, the sterile plug junction (25) is attached to the bioreactor's inoculation port. The cut, washed roots are then resuspended in 300 ml growth medium from the reactor using the peristaltic pump. The pump is then stopped and the cut root inoculum poured into the reactor via the inoculum outlet (17), outlet tube (23) and sterile plug junction (25) by tilting the inoculation vessel. The inoculation vessel is then filled with fresh growth medium from the bioreactor in case of root pieces remaining in the inoculation vessel. The last two steps are repeated as often as needed for complete transfer of the hairy or adventitious root pieces of the inoculum into the bioreactor. Then, all tubes (22, 23, and the tube leading to 24) are pinched off and the inoculation vessel is disconnected from the bioreactor.

2. Determination of Viability and Growth of Hairy Roots Upon Manual Cutting

It had been shown that cutting hairy roots leads to growth inhibition (Krombholz et al., Planta Medica 58(34): 328-333, 1 Aug. 1992). However, cutting, especially mechanical cutting, vastly improves ease and efficiency of inoculation as well as harvesting of root organ cultures, especially of scalable root organ cultures. Therefore, the inventors designed a study to determine whether cutting to certain fragment sizes could be tolerated by hairy roots, and, if so, what the minimal viable fragment length for hairy roots was.

For this purpose, a hairy root culture was manually cut into fragments of 2 mm or 12 mm length before cultivation of these fragments on petri-dishes filled with solidified medium. Cultivation on solidified medium allowed for monitoring of each fragment across the entire length of culturing. Fragments were divided into shoot tips and mid-fragments depending on their origin within the larger predecessor hairy roots obtained from the initial culture. For example, a 20 mm predecessor root can be cut into 2 shoot tip fragments (corresponding to those fragments encompassing the tips of the predecessor root) and 8 mid-fragments, each of 2 mm size. The fragment lengths were assessed per hand after 12 days of cultivation on solidified medium, and a second time after 20 d of cultivation on solidified medium.

Figure 7:
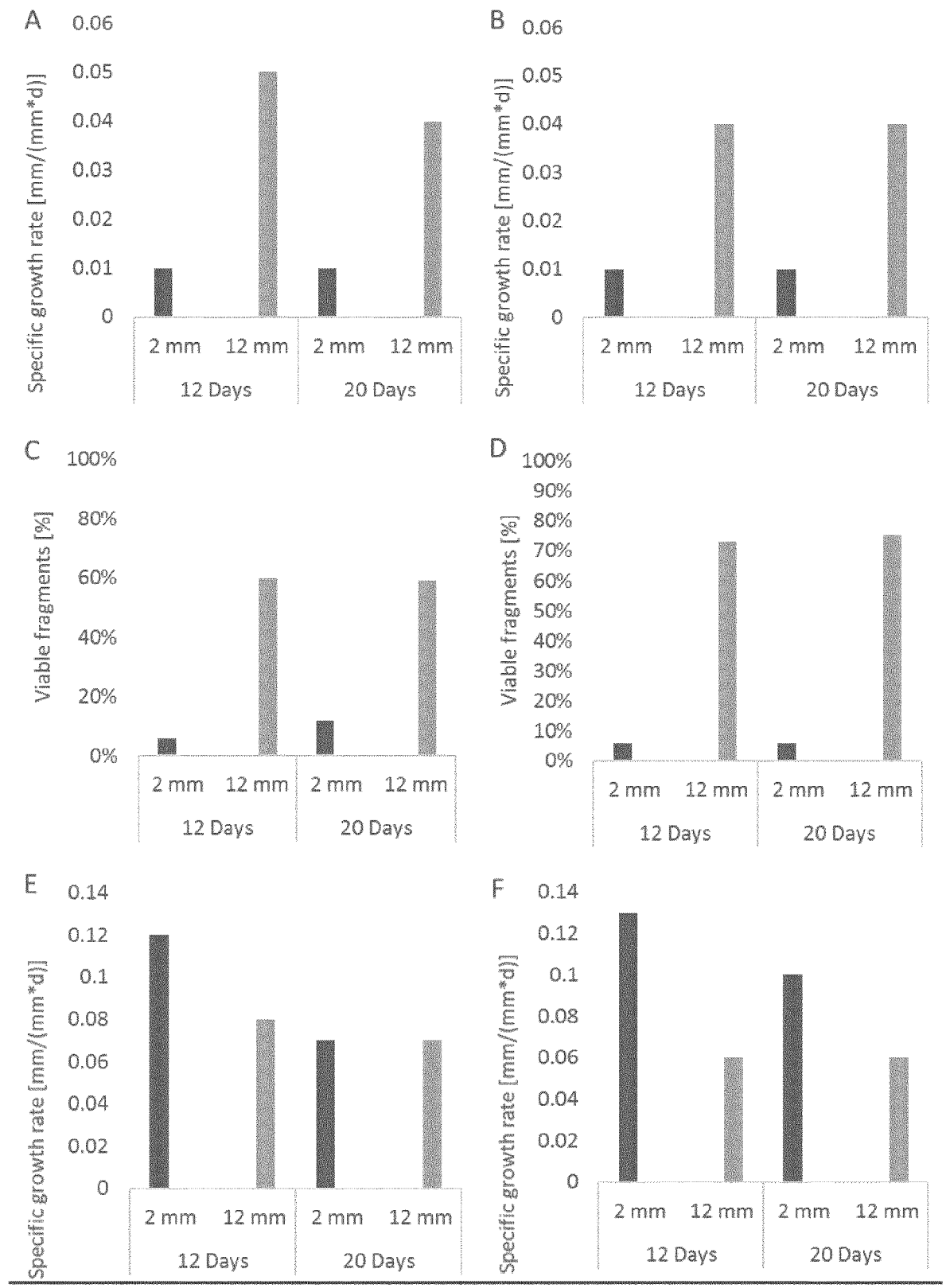
FIG. 7 shows growth evaluations of manually cut hairy root fragments of either 2 or 12 mm length after 12 or 20 days of cultivation on solid culture medium. A, C, and E depict shoot tip growth. B, D, and F depict mid-fragment growth. A, B: average growth rate in mm/d (N=12). C, D: viable fragments as % of total fragments. E, F: average growth rate of viable fragments only in mm/d.
Figure 8:
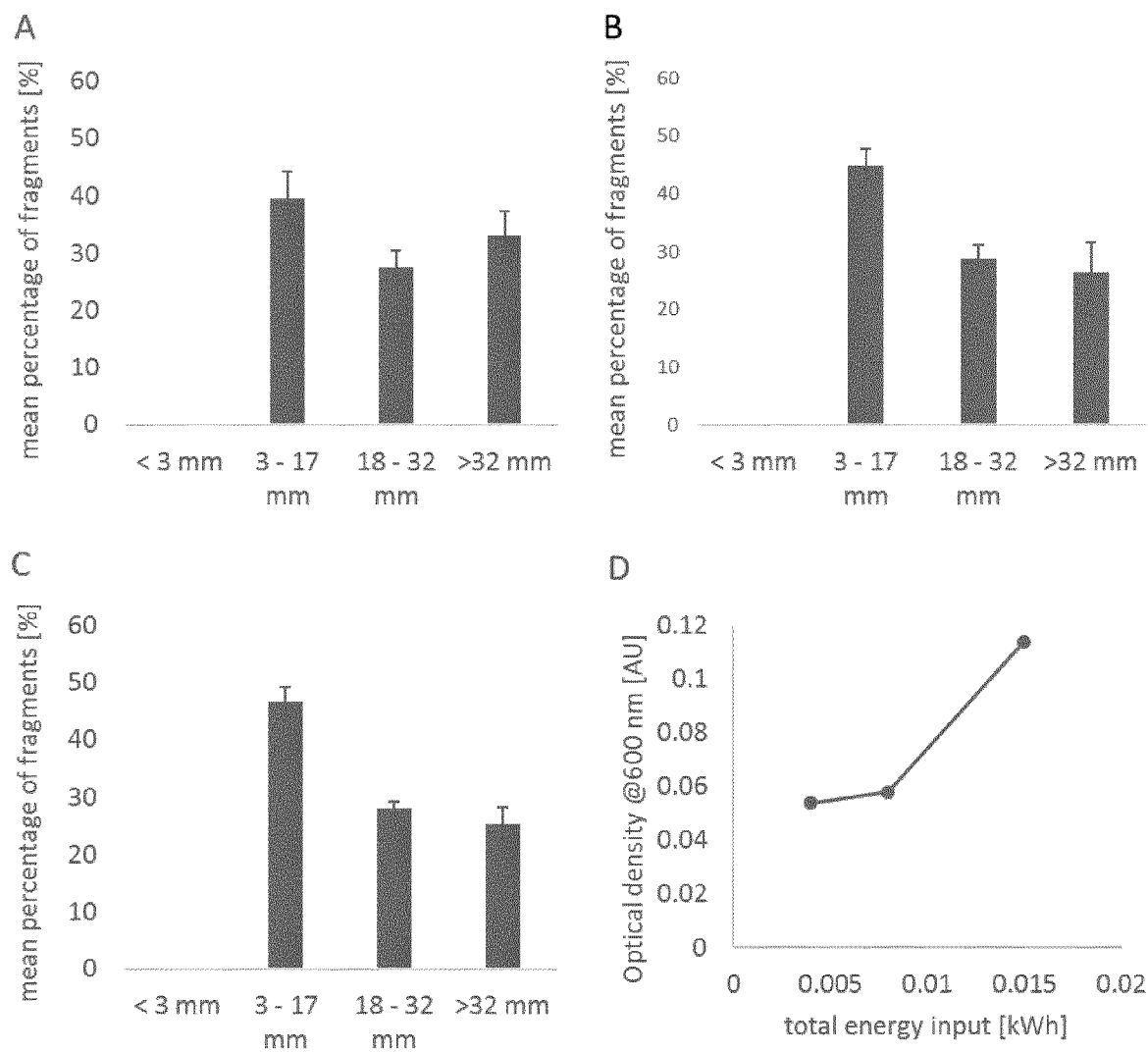
FIG. 8 shows fragment size evaluation of different automated hairy root homogenization experiments. Error bars depict the standard deviation of 3 technical replicates. A: Fragment size (in mm) distribution at lowest tested power input, of 0.0008 kWh/g. B: Fragment size (in mm) distribution at medium tested power input, of 0.0016 kWh/g. C: Fragment size (in mm) distribution at highest tested power input, of 0.003 kWh/g. D: Optical density at 600 nm of the liquid phase of the homogenized cultures at the three tested power inputs.

FIG. 7 shows the results of this study, with FIGS. 7A, C, and E depicting shoot tip growth, and FIGS. 7B, D, and F depicting mid-fragment growth. Average growth rates were greater for 12 mm fragments than for 2 mm fragments regardless of the origin of the fragments within the predecessor roots (see FIG. 7A, B). Further, viability of 2 mm pieces ranged from only 6%-12%, while viability of 12 mm pieces ranged from 60%-75% (see FIG. 7C, D). Notably, the 12 mm mid-fragment fragments (FIG. 7D) have the highest proportion of viable pieces (73-75%). Accordingly, cutting hairy root fragments to 2 mm substantially impairs their viability, while cutting them to 12 mm pieces preserves a sufficient amount of viable fragments.

Surprisingly, the highest observed growth rates were for viable 2 mm fragments (see FIG. 7E, F), however, the high amount of dead biomass obtained when cutting to fragments to 2 mm size renders cutting hairy root biomass to fragments of 2 mm or below in length unsuitable for achieving high biomass productivities (confirming earlier observations that cutting leads to growth impairment of hairy roots), since in liquid culture and/or with automated cutting, no sorting for viable fragments is possible, and since the considerable effort going into manual cutting and sorting is not feasible for larger scale solid cultures. Importantly however, cutting to larger fragments, e.g. 12 mm and above, yields suitable hairy root biomass for liquid culture inoculation into any scale bioreactor.

3. Determination of Hairy Root Fragment Length Upon Various Automated Cutting Regimens Having determined the minimal feasible length for cutting hairy root fragments in Example 2, the inventors set out to determine an automated cutting regimen using a fast rotatable knife or rotor stator homogenizer within an inoculation vessel or bioreactor that would improve scalability, ease, and effectiveness by foregoing manual cutting in an aseptic environment. Specifically, the inventors sought to determine if and how hairy roots can be cut into fragments using an automated cutting device (e.g. fast rotatable knife or rotor stator homogenizer) to achieve fragments of above 2 mm in length.

The experimental setup corresponded to FIG. 6, i.e. an inoculation vessel comprising a fast rotatable knife homogenizer (see FIG. 6), into which were filled hairy root clump aliquots of 5 g fresh weight (FW) suspended in 200 ml growth medium. After pre-experimentation to set up the minimal power for fragmentation of these hairy root clumps, three different homogenization regimens, distinguished by their total power input (e.g. homogenization time) were tested in triplicate homogenizations, namely 0.0008 kWh/g, 0.0016 kWh/g and 0.003 kWh/g. The resulting fragment size for these homogenization regimens were analysed, and the fragment size distribution was evaluated. As fragments of 2 mm length or below could not be reliably quantified by manual counting because of the high number of fragments, the optical density (OD) of the liquid phase after homogenization was measured as well. This OD measurement at 600 nm served to estimate the amount of liberated cells and/or small particles in the suspension, i.e. served as an estimate for tissue damage of the roots suffered as a consequence of the homogenization. The higher the OD, the more small tissue particles and/or cells have been separated from the root biomass and have gone into suspension. These small tissue particles and/or liberated cells are not considered viable biomass suitable for root organ culture inoculation. Accordingly, higher OD values mean impaired culture growth.

Fragmentation was successfully achieved for all homogenization regimens and the obtained fragment size distribution was highly reproducible despite the inhomogeneous nature of hairy root clumps (see FIG. 3A-C). The lower total energy input regimens lead to bigger fragment sizes (see FIG. 3A-C) and lower optical densities (see FIG. 3D)—meaning lower amount of tissue damage, and higher viability of the roots. There was no further decrease in size observed when upping the power input above that of regimen 2 (compare FIG. 3B with FIG. 3C), but the optical density of the supernatant did increase (see FIG. 3D), indicating further decreased viability of the obtained fragments.

Accordingly, the lowest energy input homogenization regimen (total energy input $<8*10^-4$ kWh/g BM FW) led to viable fragments of hairy roots suitable for hairy root culture inoculation/harvest, demonstrating that mechanical homogenization before, during, or after root organ culture is feasible for hairy root cultures.

4. Comparison of Different Bioreactors of the Invention with Conventional Bioreactors Bioreactors of the invention were compared to a standard bioreactor to assess improvements to total biomass yield and effective biomass yield, i.e. that biomass yield which is harvestable by automation without use of an aseptic environment to prevent contamination of the biomass.

Figure 9:
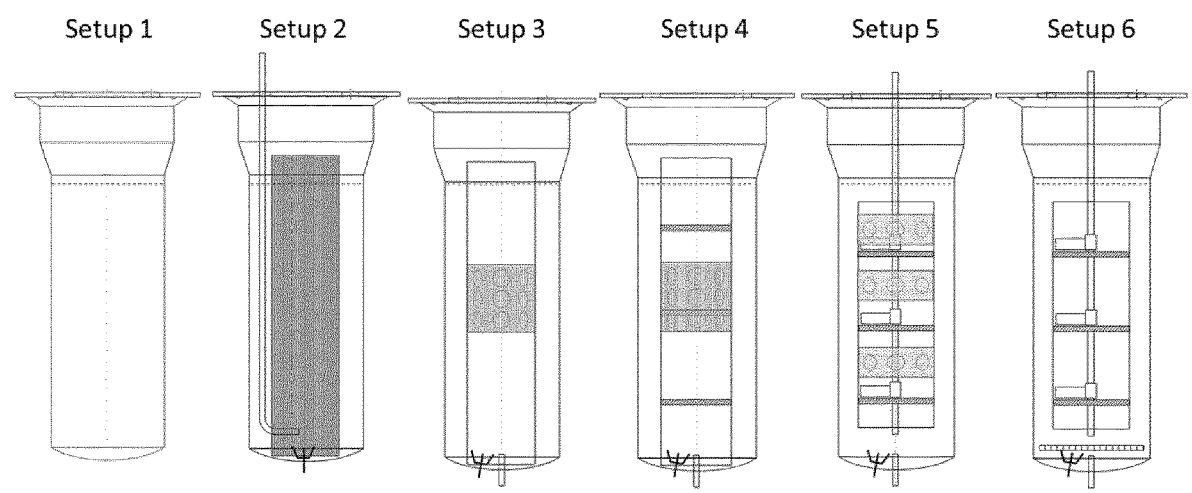
FIG. 9 shows schematic depictions of interior elements of different bioreactors. All bioreactors had a working volume of 3 L and featured a cultivation chamber an inoculation port with an inner diameter of 10 mm; a harvest port (5) with an inner diameter 10 mm located at the bottom of the bioreactor, and two aeration outlets. Setups 2-6 also featured a fast rotatable knife or rotor stator located at the bottom of the bioreactor. Setup 2 further featured an attachment matrix and a submersion pipe with a sintered metal sparger frit. Setup 3 featured no attachment matrix, but a draft-tube extending above the level of the culture medium during culture. Setup 4 featured a draft-tube extending above the level of the culture medium during culture, an attachment matrix composed of three horizontal root support disks separating the space within the draft tube into four compartments, and a sintered metal sparger frit at the bottom of the reactor. Setup 5 featured a draft-tube completely submerged in the culture medium during culture, an attachment matrix composed of three horizontal root support disks separating the space within the draft tube into four compartments, three detachment knives mounted horizontally on a central vertical rotary shaft, and a sintered metal sparger frit at the bottom of the reactor. Setup 6 featured a draft-tube completely submerged in the culture medium during culture, an attachment matrix composed of three horizontal root support disks separating the space within the draft tube into four compartments, three detachment knives mounted horizontally on a central vertical rotary shaft, and a ring below the bottom end of the draft tube.

Six different bioreactors were tested (see FIG. 9 for schematic depictions of interior elements of the 6 bioreactors), wherein Setup 1 was a standard bioreactor, and Setups 2-6 were bioreactors of the invention. All bioreactors had a working volume of 3 L and featured a cultivation chamber, an inoculation port with an inner diameter of 10 mm; a harvest port (5) with an inner diameter 10 mm located at the bottom of the bioreactor, and two aeration outlets. Setups 2-6 also featured a fast rotatable knife or rotor stator located at the bottom of the bioreactor.

Setup 2 further featured an attachment matrix and a submersion pipe with a sintered metal sparger frit attached at the submerged end. The attachment matrix consisted of a tubular shaped steel mesh (stainless steel 316L, perforation: Rv 4-6 DIN 24041). The attachment matrix cylinder was 450 mm high and 65 mm in diameter. It was placed on the bottom of the bioreactor with screws concentrically attached as spacers from the bioreactor wall. Air was introduced from the bottom side of the attachment matrix cylinder via the submersion pipe and sintered metal sparger frit.

Setup 3 featured no attachment matrix, but a draft-tube extending above the level of the culture medium during culture. The draft-tube separated the hairy root fragments from all further bioreactor inserts (e.g. submersion tube, sparging frit, etc.). The draft tube's purpose was to simulate a separate cultivation chamber within the main cultivation chamber, in which no interference of other reactor inserts with the hairy root biomass could occur. The draft tube consisted of a polycarbonate (PC) tube (height: 450 mm, outside diameter: 70 mm, wall thickness: 3 mm) with drill holes in three rows (200 mm from the top end) and a steel mesh (50 µm mesh size) covering the holes. The drill holes served the purpose of medium circulation from the culture volume inside of the draft tube to the other bioreactor inserts located outside of the draft tube. The mesh size did not allow root fragments to pass through the drill holes or attach thereto. Therefore, Setup 3 did not contain an attachment matrix. The tube was placed on the reactor bottom, reaching above the liquid level. Air was introduced from the vessel's bottom via a sintered metal sparger frit through a central outlet.

Setup 4 featured a draft-tube extending above the level of the culture medium during culture, an attachment matrix composed of three horizontal root support disks separating the space within the draft tube into four compartments, and a sintered metal sparger frit at the bottom of the reactor. The three root support disks were equally spaced from each other and consisted of perforated steel plates (stainless steel 316L, 64×64 mm, thickness: 1.5 mm, mesh size: 5×5 mm). They were mounted through slits in the draft tube, which was otherwise constructed as in Setup 3. The root support disks reached throughout the draft tube's entire diameter, thereby forming a platform and surface for root fragment attachment. The draft tube was placed on the bioreactor bottom as in Setup 3, reaching over the top of the liquid level. Accordingly, the space within the draft tube was divided into four equally sized compartments, which served to distribute the biomass more evenly over the culture volume. Air was supplied from the central sintered metal sparger at the bottom of the bioreactor. For this setup, 3 replicate experiments were performed Setup 5 featured a draft-tube completely submerged in the culture medium during culture, an attachment matrix composed of three horizontal root support disks separating the space within the draft tube into four compartments, three detachment knives mounted horizontally on a central vertical rotary shaft, and a sintered metal sparger frit at the bottom of the reactor. The draft tube and root support disks of the attachment matrix were constructed as in Setup 4, with the difference that the draft tube did not extend above the culture medium level during culture. The detachment knives were used both during inoculation in order to improve biomass distribution due to their rotation, and at the end of culturing for root detachment from the root support disks.

Setup 6 featured a draft-tube completely submerged in the culture medium during culture, an attachment matrix composed of three horizontal root support disks separating the space within the draft tube into four compartments, three detachment knives mounted horizontally on a central vertical rotary shaft, and a sparger consisting of two sparging elements, one of which was a central frit located centrally below the draft tube and one of which was a ring sparger located above the sparging frit and below the bottom end of the draft tube. By gassing through the ring sparger, a different flow pattern in the bioreactor is achieved to increase biomass distribution throughout the culture volume. The draft tube, root support disks of the attachment matrix, and detachment knives were identical to Setup 5, with the exception of the absence of drill holes in the draft tube. For this setup, 3 replicate experiments were performed Cultures were inoculated with a 300 ml inoculum containing 8-20 g fresh weight biomass consisting of cut hairy root fragments, and cultured for 15-42 days. Where the bioreactors contained a sparger, the air flow rate during inoculation and culturing was set to 10-15 sL/h.

Figure 10:
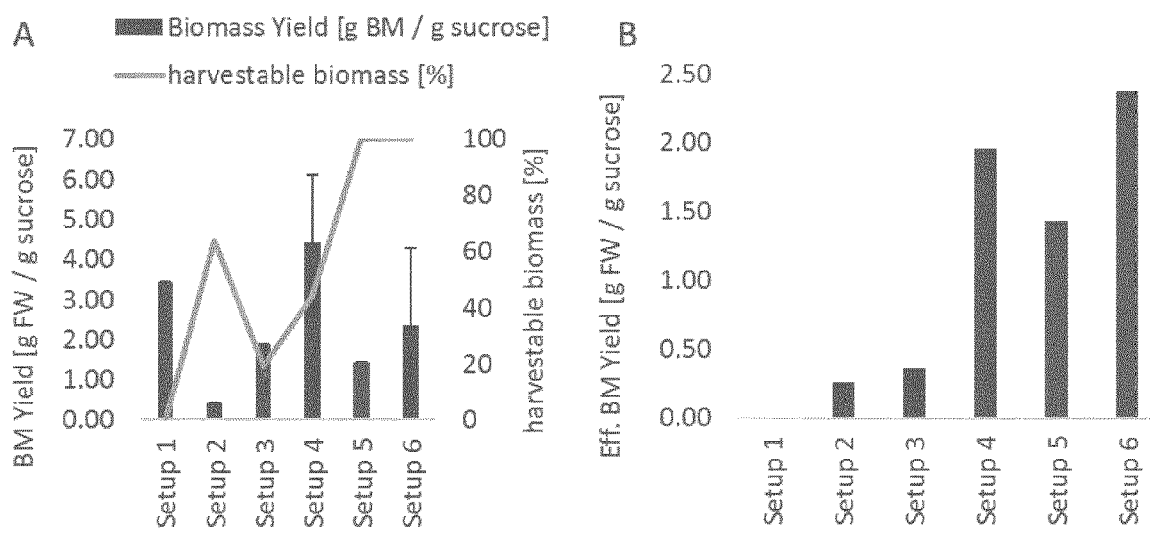
FIG. 10 shows biomass yield and harvestable biomass percentage analysis of hairy root cultures cultured in the different bioreactors depicted in FIG. 9. Cultures were inoculated with 8-20 g fresh weight biomass consisting of cut hairy root fragments and cultured for 15-42 days. Where the bioreactors contained a sparger, the air flow rate during inoculation and culturing was set to 10-15 sL/h. A: Total biomass yield calculated from final biomass at the end of culturing (fresh weight; in grams) divided by metabolized sucrose (in grams) shown as black bars, harvestable biomass in % of total biomass at the end of culturing shown as grey line. Error bars for setups 4 and 6 show the standard deviation for 3 technical replicates. B: Effective biomass yield calculated by multiplying the total biomass yield and harvestable biomass from A.

At the end of culturing, final biomass fresh weight and total sucrose metabolized during culture were measured in grams. Further, the final biomass fresh weight was divided into harvestable and non-harvestable biomass. Biomass attached to attachment matrices and biomass in suspension was considered (mechanically) harvestable biomass, whereas biomass attached to reactor built-ins other than attachment matrices, e.g. spargers, walls, etc., was not considered harvestable, as the bioreactors have to be opened for manual harvest, requiring a sterile environment. Biomass yield, i.e. total final biomass (fresh weight; in grams) divided by metabolized sucrose (in grams) varied between the bioreactors, with setups 1 and 4 showing highest yields (see FIG. 10A, black bars). In contrast, mechanically harvestable biomass was zero for setup 1 (the standard bioreactor), and varied between 20 and 100% of total biomass yield for the bioreactors of the invention (see FIG. 10A, grey line). Setups 5 and 6 are especially favorable in terms of harvestable biomass, with both achieving a mechanical harvest of 100% of the total yield.

Finally, the effective biomass yield, i.e. the mechanically harvestable biomass yield (fresh weight) divided by the metabolized sucrose, was calculated by multiplying the total biomass yield and harvestable biomass percentage. All bioreactors according to the invention show higher effective biomass yields than the standard bioreactor of Setup 1, with Setups 4-6 being the most efficient (see FIG. 10B).

The invention claimed is:

1. A bioreactor for the cultivation of hairy roots, comprising:
  a cultivation chamber (2);
  a rotor stator (6) for cutting the hairy roots located at the bottom of the bioreactor;
  an inoculation port (1), wherein the inner diameter of the inoculation port (1) is ≥10 mm;
  a harvest port (5), wherein the inner diameter of the harvest port (5) is ≥10 mm and wherein the harvest port (5) is located at the bottom of the bioreactor; and
  two aeration outlets (3, 4), wherein one aeration outlet is for gas inlet and the other aeration outlet is for gas outlet;
  optionally further comprising
  a gas sparger (7), wherein the one aeration outlet for gas inlet is connected to the gas sparger (7),
  one to four outlets for dip tubes (8), wherein the one to four dip tubes are for base addition, feed addition, acid addition, and/or sampling, and/or
  one to three ports for probes (9), wherein the probes are for measuring pH, dissolved oxygen, and/or conductivity.

2. The bioreactor of claim 1, further comprising
  an attachment matrix (10a);
  a rotatable attachment matrix mounting (12);
  a vertical shearing blade (11a) for root detachment; and
  a support ring for the shearing blade (13);
wherein the attachment points on the attachment matrix (10a) are vertically arranged, and wherein the attachment matrix (10a) is vertically rotatable on the rotatable attachment matrix mounting (12) and the vertical shearing blade (11a) is static.

3. The bioreactor of claim 1, wherein the bioreactor does not comprise an attachment matrix.

4. The bioreactor of claim 1, further comprising an attachment matrix (10b), wherein the attachment matrix (10b) is composed of beads, said beads comprising a polysaccharide and a growth medium.

5. The bioreactor of claim 1, further comprising an attachment matrix (10c); a central, vertical rotary shaft; and multiple horizontally arranged detachment knives (11b); wherein the attachment matrix (10c) is composed of multiple, horizontal root support disks, and wherein said root support disks are spaced in regular distances of ≥10 cm, and wherein the detachment knives (11b) are mounted horizontally on the vertical rotary shaft so that one detachment knife (11b) is located at a distance of 0.05-5 mm from each root support disk, and wherein the number of detachment knives (11b) is the same as or larger than the number of root support disks.

6. The bioreactor of claim 5, further comprising a cylindrical draft tube (14), wherein the horizontal root support disks are mounted inside of the cylindrical draft tube (14), wherein the cylindrical draft tube (14) consists of a cylinder that is fully open at its top and bottom ends, and wherein the gas sparger (7) consists of one sparging element, optionally of two independently usable sparging elements, one of which (7a) is located beneath the center of the draft tube and the other one of which (7b) is a ring sparger located either below or outside the draft tube in the bottom half of the cultivation chamber.

7. A method of producing and aseptically harvesting hairy roots, comprising the steps of
  1) cultivating a hairy root culture in a growth medium inside the bioreactor of claim 1;
  2) optionally detaching the hairy roots of the hairy root culture from an attachment matrix inside the bioreactor;
  3) Optionally letting the hairy roots settle;
  4) Cutting the hairy roots inside the bioreactor using the rotor stator (6) at the bottom of the bioreactor; and
  5) Removing the cut hairy roots using the harvest port (5);
wherein steps 1-4 are performed inside the bioreactor and wherein steps 1-5 do not require an aseptic environment.

8. The method of claim 7, wherein the bioreactor further comprises an attachment matrix (10a), a rotatable attachment matrix mounting (12), a vertical shearing blade (11a) for root detachment, and a support ring for the shearing blade (13),
  wherein
    the attachment points on the attachment matrix (10a) are vertically arranged,
    the attachment matrix (10a) is vertically rotatable on the rotatable attachment matrix mounting (12) and the vertical shearing blade (11a) is static, and
    the detaching step is accomplished by the use of shear force exerted by the shearing blade (11a) on the rotating matrix.

9. The method of claim 7, wherein the bioreactor does not comprise an attachment matrix,
  wherein the cultivating step comprises inducing culture media movement by gassing the hairy root culture at 0.2-50 sL/L/h throughout the step of cultivating, and wherein the gassing is done by the gas sparger (7).

10. The method of claim 7, wherein the bioreactor further comprises an attachment matrix (10b), wherein the attachment matrix (10b) is composed of beads, said beads comprising a polysaccharide and a growth medium, and wherein the detaching step is accomplished by dissolving the attachment matrix (10b) beads, optionally wherein the attachment matrix (10b) beads are dissolved by addition of citric acid or a polysaccharide cleaving enzyme.

11. The method of claim 7, wherein the bioreactor further comprises an attachment matrix (10c), a central, vertical rotary shaft, and multiple horizontally arranged detachment knives (11b),
  wherein
    the attachment matrix (10c) is composed of multiple, horizontal root support disks,
    said root support disks are spaced in regular distances of ≥10 cm,
    the detachment knives (11b) are mounted horizontally on the vertical rotary shaft so that one detachment knife (11b) is located at a distance of 0.05-5 mm from each root support disk,
    the number of detachment knives (11b) is the same as or larger than the number of root support disks, and
    the detaching step is accomplished by the use of shear force exerted by the detachment blades (11b) rotating above the root support disks.

12. The method of claim 7, wherein the cutting step is accomplished by the rotor stator (6) at the bottom of the bioreactor, optionally wherein the cutting step is performed at a temperature of 0-35° C., and/or optionally wherein the removing step is accomplished using a peristaltic pump, a chopper pump, or a screw conveyor or by flushing with growth medium.

13. An apparatus for inoculation, cultivation, and harvest of hairy root cultures, comprising
a first bioreactor of claim 1, and
at least one further bioreactor of claim 1, wherein said first bioreactor is connected to said at least one further bioreactor.

14. A method of producing hairy roots, comprising
(a) a method of preparing an inoculum for a hairy root culture from viable hairy root biomass, comprising the following steps:
1) Introducing viable hairy root biomass into the first bioreactor of the apparatus of claim 13 via the inoculation port (1) in an aseptic environment,
2) Optionally cultivating the introduced hairy root biomass in the presence of a growth medium,
3) Optionally cutting the hairy root biomass with the rotor stator (6) of the first bioreactor, and
4) Transferring the inoculum and/or cut inoculum from the first bioreactor of the apparatus of claim 13 to the at least one further bioreactor using the harvest port (5) of the first bioreactor and the inoculation port (1) of the at least one further bioreactor,
wherein steps 2 and 3 are performed inside the first bioreactor, and wherein steps 2 to 4 do not require an aseptic environment;
followed by
(b) the method of producing and aseptically harvesting hairy roots comprising the steps of
5) Cultivating a hairy root culture in a growth medium using the at least one further bioreactor, wherein the first bioreactor and the at least one further bioreactor are comprised in the apparatus of claim 13,
6) Optionally detaching the hairy roots of the hairy root culture from an attachment matrix inside the at least one further bioreactor,
7) Optionally letting the hairy roots settle,
8) cutting the hairy roots inside the at least one further bioreactor using or the rotor stator (6) at the bottom of the at least one further bioreactor, and
9) Removing the cut hairy roots using the harvest port (5),
wherein steps 5-8 are performed inside the at least one further bioreactor and wherein steps 5-9 do not require an aseptic environment.

15. An apparatus for inoculation, cultivation, and harvest of hairy root cultures, comprising
(a) an inoculation vessel for preparing an inoculum for a hairy root culture from viable hairy root biomass, comprising:
an inoculation chamber (21);
a knife (16), wherein the knife (16) is part of a rotatable stirrer blade construction or a knife mill construction and wherein the knife (16) is located within the chamber (21); and
between three and five outlets from the chamber, wherein the outlets are for root biomass inlet (15), inoculum outlet (17), aeration, media inlet, and media outlet,
and
(b) the bioreactor of claim 1, wherein said inoculation vessel is connected to said bioreactor.

16. A method of producing hairy roots, comprising
(a) a method of preparing an inoculum for a hairy root culture from viable hairy root biomass, comprising the following steps:
1) Introducing viable hairy root biomass into the inoculation vessel of the apparatus of claim 14 via one of the three to five outlets in an aseptic environment,
2) Cutting the hairy root biomass with the knife (16) of the inoculation vessel,
3) optionally washing the cut hairy root biomass with a washing medium using one or more of the three to five outlet(s) of the inoculation vessel for media inlet and media outlet, and
4) Transferring the cut, optionally washed, inoculum from the inoculation vessel to the bioreactor of the apparatus of claim 14 using one of the three to five outlets for inoculum outlet (17),
wherein steps 2 and 3 are performed inside the inoculation vessel, and wherein steps 2 to 4 do not require an aseptic environment;
followed by
(b) the method of producing and aseptically harvesting hairy roots comprising the steps of
5) Cultivating a hairy root culture in a growth medium using the bioreactor,
6) Optionally detaching the hairy roots of the hairy root culture from an attachment matrix inside the bioreactor,
7) Optionally letting the hairy roots settle,
8) cutting the hairy roots inside the bioreactor using the rotor stator (6) at the bottom of the bioreactor, and
9) Removing the cut hairy roots using the harvest port (5),
wherein steps 5-8 are performed inside the bioreactor and wherein steps 5-9 do not require an aseptic environment.

* * * * *